United States Patent [19]

Arulanandan

[11] 4,219,776
[45] Aug. 26, 1980

[54] METHOD AND APPARATUS FOR MEASURING IN SITU DENSITY AND FABRIC OF SOILS

[75] Inventor: Kandiah Arulanandan, Davis, Calif.

[73] Assignee: The Regents of The University of California, Berkeley, Calif.

[21] Appl. No.: 936,836

[22] Filed: Aug. 25, 1978

Related U.S. Application Data

[63] Continuation-in-part of Ser. No. 910,577, May 30, 1978, abandoned, which is a continuation-in-part of Ser. No. 831,877, Sep. 9, 1977, abandoned.

[51] Int. Cl.$^2$ .................. G01V 3/06; G01R 27/00
[52] U.S. Cl. .................. 324/323; 324/61 P; 324/65 P; 324/324; 324/355
[58] Field of Search .................. 324/1, 2, 10, 11, 13, 324/30 B, 57 R, 61 P, 65 P, 62, 60 R

[56] References Cited

U.S. PATENT DOCUMENTS

| | | | |
|---|---|---|---|
| 2,082,213 | 6/1937 | O'Donnell | 324/30 R |
| 2,228,223 | 1/1941 | Bays | 324/10 X |
| 2,766,421 | 10/1956 | Wait et al. | 324/1 |
| 2,786,977 | 3/1957 | Blagg et al. | 324/13 X |
| 2,793,527 | 5/1957 | Turner et al. | 324/65 P |
| 2,870,404 | 1/1959 | Oxley | 324/65 P |
| 2,968,180 | 1/1961 | Schafer | 324/57 R X |
| 2,972,106 | 2/1961 | Hyrne | 324/57 R |
| 3,034,044 | 5/1962 | Konigsberg | 324/57 R |
| 3,617,868 | 11/1971 | Beitel | 324/13 |
| 3,895,289 | 7/1975 | Rickey et al. | 324/13 X |
| 3,975,676 | 8/1976 | Bliamptis | 324/9 |

*Primary Examiner*—Gerard R. Strecker
*Attorney, Agent, or Firm*—Owen, Wickersham & Erickson

[57] ABSTRACT

A method and implementing apparatus for measuring in situ the electrical capacitance and resistance of soils and determining therefrom the density and fabric thereof. The apparatus includes a self-contained probe adapted to be driven into the soil to be measured. The probe has a soil sensor element and a measuring circuit such as a capacitance and resistance bridge. The measuring circuit employs radiofrequency current to enable direct measurement at the probe of the resistance and capacitance of the soil sample and of the pore liquid. A remote indicator and control unit in communication with the probe is provided with indicators such as meters or displays which provide direct readout of measured resistance and capacitance, and which may also enable the bridge in the probe to become balanced. Alternatively, the probe may include a computer for automatically balancing the bridge and calculating critical soil properties. The apparatus can automatically register such engineering properties as density, porosity, friction angle, elastic and secant modulus, coefficient of dynamic settlement, stress ratio required to cause liquefaction, and permeability coefficient. The probe and measuring equipment can, alternatively, be manually balanced and the engineering properties and related properties can be hand calculated. The concept outlined and apparatus can be extended or modified for a wide variety of other uses also.

54 Claims, 16 Drawing Figures

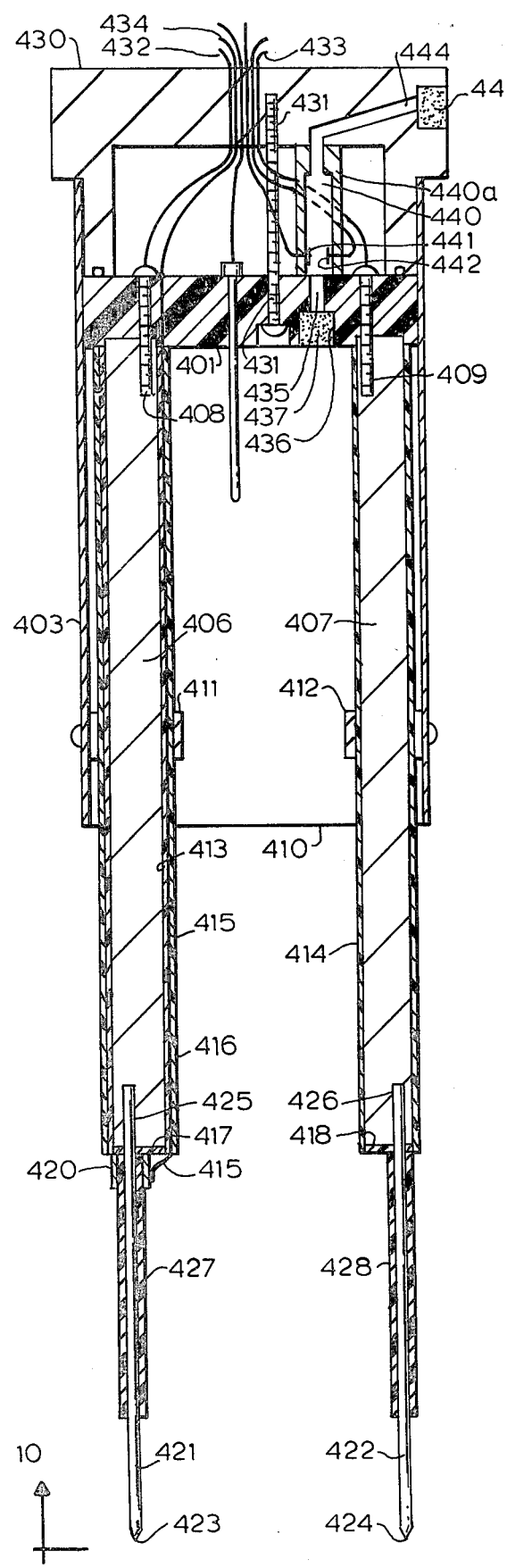
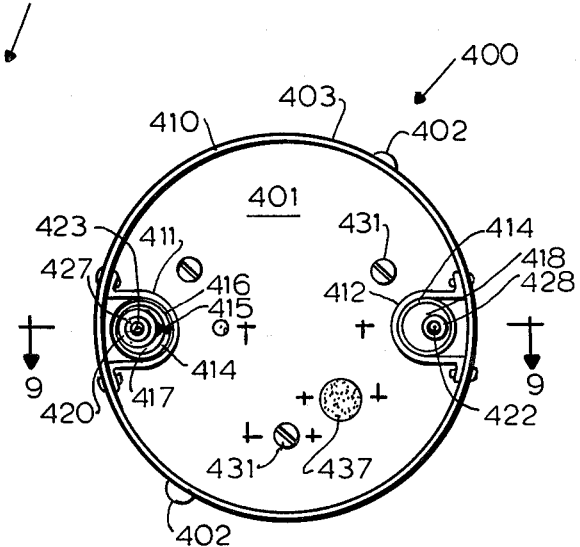
FIG. 9
FIG. 10

RELATIONSHIP BETWEEN STRESS RATIO REQUIRED TO CAUSE LIQUEFACTION IN 10 CYCLES AND THE STRUCTURE INDEX, $I_F$, FOR VARIOUS SANDS AND METHODS OF PLACEMENT.

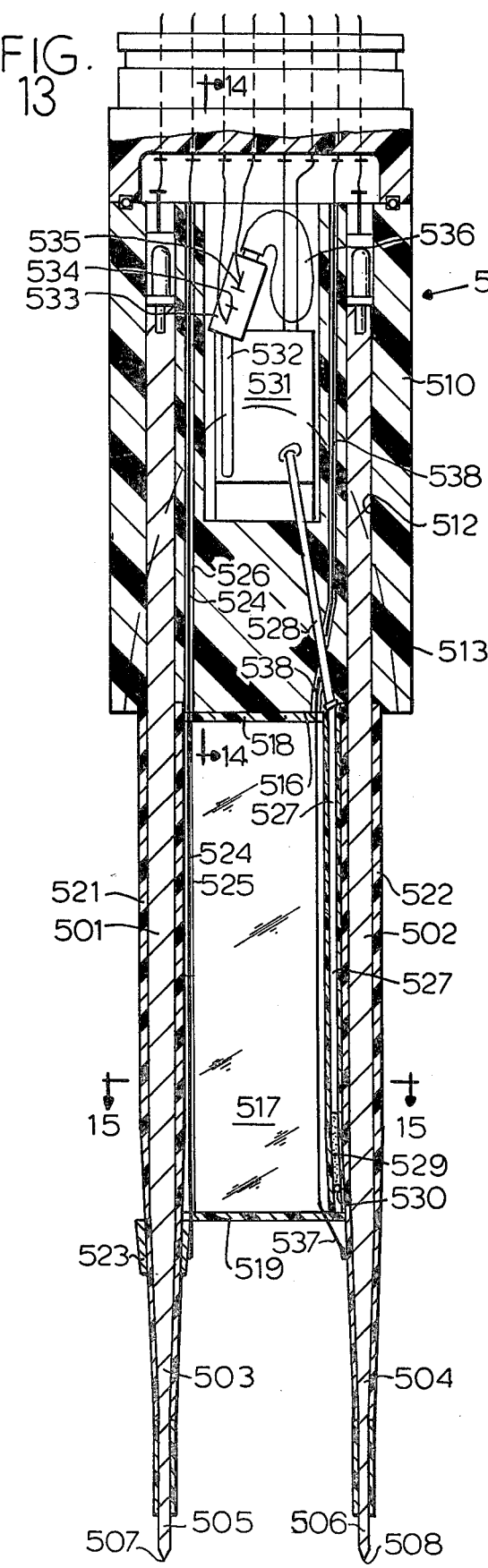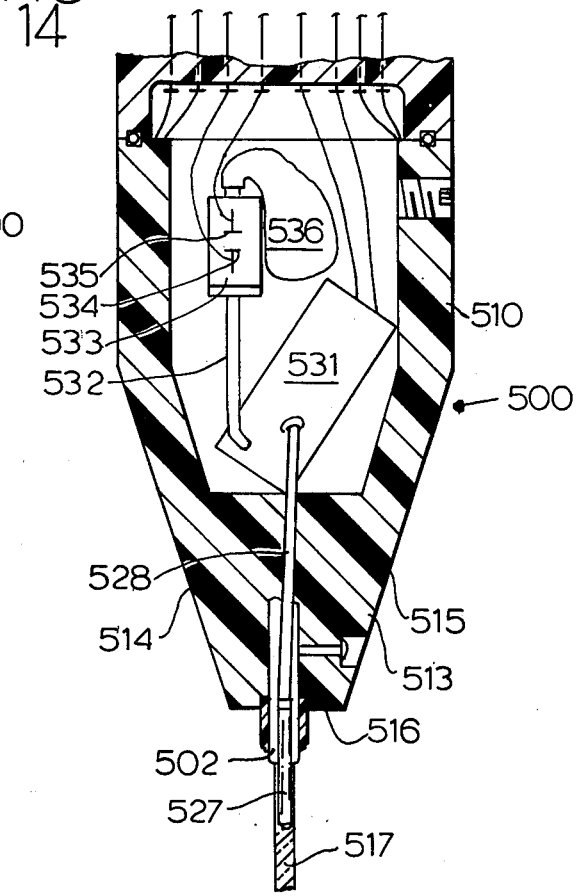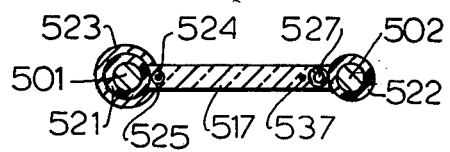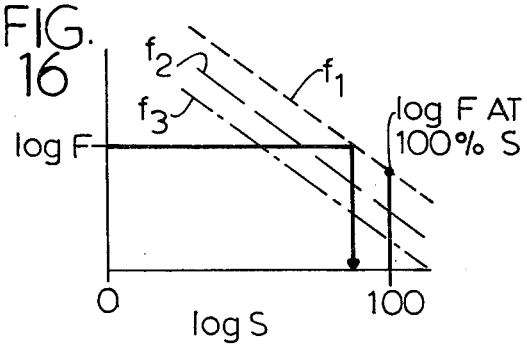

METHOD AND APPARATUS FOR MEASURING IN SITU DENSITY AND FABRIC OF SOILS

REFERENCE FOR CO-PENDING APPLICATION

This invention is a continuation-in-part of application Ser. No. 910,577, filed May 30, 1978, now abandoned which was a continuation-in-part of application Ser. No. 831,877, filed Sept. 9, 1977, now abandoned.

BACKGROUND OF THE INVENTION

The present invention relates to method and apparatus for determining in situ the density and fabric or structure of soils, sands, silts, and other materials. More particularly, the present invention provides a method and implementing apparatus for measuring in situ the electrical capacitance and resistance of soil samples at a predetermined depth and determining therefrom the density and fabric or structure of the soil. Other uses are also indicated.

A knowledge of the in situ density and structure of sands, loams, and silts is necessary for the accurate prediction of the settlement and liquefaction potentials of these soils. A recognition of the danger of these soils behaving as a liquid in earthquakes has brought about a practical requirement that the liquefaction potential of all natural deposits and fills of soils be evaluated for all construction projects.

It has been generally understood that the behavior of granular media, such as soils, sands, loams, silt, and other material, depends mainly on overall structure rather than the properties of each individual grain. With sands, for example, an average size range of the grains may be determined; whereupon the term "structure" (sometimes called "fabric") is related to three basic features: the shape of the solid particles, the spatial arrangement of the solid particles, and the associated voids. While it has been recognized that these three basic features must be taken into account in any index used to quantify sand structure, the practical results have not been satisfactory.

Porosity alone, for example, is known to be inadequate. Relative density has proven a better index than porosity, but has dual drawbacks found (1) in difficulty of evaluating its value accurately and (2) in variation of properties resulting from different methods of preparation of sand samples.

A common disadvantage shared by the indices of, e.g., porosity and relative density is that they are scalar quantities not associated with any particular direction in the sample. Hence, they cannot possibly account for the anisotropic character of the sand mass resulting from the shapes and spatial arrangements of the solid particles.

Electrical methods have been used in the past to determine the density of sands. H. Camberfort, in his paper entitled "In Situ Measurement of the Porosity of Sand," published in the *Proceedings of the 4th International Conference on Soil Mechanics,* London, 1957, at pages 213-215, sets forth an empirical equation which related the void ratio (e) of sand to the resistivity of the sand-solution mixture (P), and the resistivity of the pore fluid ($P_0$), that is, the fluid in the interstices or pores of the soil. That empirical equation was:

$$e = \frac{1.56}{(P/P_0 - 1)} \quad (1)$$

where $P/P_0$ was defined as the "Formation Factor", F. According to Camberfort's equation (Equation 1), the Formation Factor (F) was only a function of the void ratio or density of sands.

It has also been shown by Fraser and Ward in their paper, "Electrical Pore Space Geometry of Porous Media," Report No. MT-63-8, July 1963, Institute of Engineering Research, Berkeley, Calif. that:

$$F = (t^2/n) \quad (2)$$

where n is the porosity and t is the tortuosity coefficient, defined as the ratio of the electrolyte path over the straight path along the direction of the measurement. In other words, the tortuosity coefficient (t) was shown to be a measure of the contortion of the path of ionic conduction due to the sand structure. Thus, the tortuosity coefficient will differ according to the shapes of the solid particles and the angle of the direction of measurement relative to the spatial arrangement of the solid particles.

G. Y. Chernyak, in his 1967 paper entitled "Dielectric Methods for Investigating Moist Soils," (translated from the Russian by N. Kaner, U.S. Department of Commerce, TT67-51258) empirically related the porosity (n) of sands to the dielectric constant (E') of the sand-solution mixture, the dielectric constant (Er) of the sand particles, and the dielectric constant (Es) of the pure fluid, in the equation:

$$Er = \frac{E'[2E' - (3n - 1)Es]}{Es + (2 - 3n)E'} \quad (3)$$

Mulilis, Seed, Chan, Mitchell, and the present inventor, in their paper entitled "Effect of Method of Sample Preparation", published in the Journal of the *Geo-Technical Engineering Division,* American Society of Civil Engineers, in February 1977, demonstrated that the fabric of sand was dictated by the method of sample preparation. Therein, soil fabric was determined by a microscopic study of thin sections obtained from a resin-impregnated sample of sand.

SUMMARY OF THE PRESENT INVENTION

It has been determined that the dielectric constant E' and formation factor F are dependent upon both the porosity and fabric of sand, silt, and loam. This dependency is formally expressed as a diminution coefficient (d). The diminution coefficient (d) is defined as the ratio of current path cross-sectional area to the sample cross-sectional area, and it characterizes the pore structure of fabric of the soil being measured. The diminution coefficient (d) is related to the porosity (n) and formation factor (F) by the expression:

$$d = \sqrt{n/F} \quad (4)$$

The dielectric constant (E') of the sand, silt, or loam solution mixture is related to the dielectric constant (Er) of the sand particles, the porosity (n), and the formation factor (F) in accordance with the following formula:

$$E' = \sqrt{n/F}(Es - Er) + Er \quad (5)$$

From this, follows:

$$n = F\left(\frac{E' - Er}{Es - Er}\right)^2 \quad (6)$$

The dielectric constants of soil particles (Er) and pore fluid (Es) are easily measurable quantities, or may be obtained from the *CRC Handbook of Chemistry and Physics*, for example. Therefore, physical measurements of the dielectric constant (E') of the soil solution mixture can be readily accomplished by measurement of the capacitance of a soil-solution mixture.

It has also been determined that the formation factor (F) at a given porosity will be different along different lines of measurement. Thus, the anisotropy (physical properties along lines of different directions) of the soil structure can be determined by measuring the formation factor (F) in different relative directions.

Thus, one method of the present invention includes the steps of (1) driving a probe having sensory elements into the soil to be tested to a fixed depth, so that the probe elements contact a sample of the soil to be evaluated, (2) balancing a bridge provided near the probe to obtain resistance and capacitance measurements for the soil sample; (3) converting the measured soil resistance and capacitance into the conductivity and dielectric constant values therefor, and (4) making similar measurements of the pore fluid from the soil at the fixed depth using the same probe. From the foregoing measurements of conductivity and dielectric constant of the soil sample, and the conductivity of the pore fluid, the formation factor (F) and porosity (n) may then be calculated, and from these parameters the engineering properties of the soil may then be determined.

The apparatus of the present invention includes a self-contained probe for being driven into the soil that is to be measured in situ. The probe includes a soil sensor element and a pore-fluid sensitive elements and a measuring circuit, such as a bridge, for enabling measurement at the probe of the electrical resistance and capacitance of the soil sample, and, then after throwing a switch, the same characteristics of the pore-fluid. One form of probe enables measurement of soil sample resistance and capacitance in at least two relative dimensions. A remote indicator and control unit in communication with the probe is provided with indicators, such as meters or displays, which provide direct readout of measured resistance and capacitance. The device may be balanced by hand or it may include a computer which automatically balances the bridge, or it may include remotely controlled adjusting devices to effectuate bridge balance.

The method and apparatus are applicable to the study of soil behavior and other geo-techniques undersea as well as on so-called dry land.

Continuous monitoring of soil behavior becomes practical, either in the natural state or during and after earthquakes and other dynamic loading conditions. Continuous monitoring of said settlement is also possible.

The invention can be used in the study of sediment deposition in estuaries. The study of the deposition and transport of solids in rivers and other bodies of water and the monitoring thereof can be achieved with the aid of this invention.

The method and apparatus are also applicable to any system which requires a knowledge of the structure and relative amounts of fluid and solid contents in the system, including processes in the food industry: for example, the fluid content, viscosity, and structure of fruits or vegetables such as tomatoes or ketchup; or the fluid content of dough and other such products.

OBJECTS OF THE PRESENT INVENTION

One object of the present invention is to provide a method and implementing apparatus for measuring phenomena of soil in situ to enable more accurate prediction of the dynamic properties thereof.

Another object of the present invention is to provide a method which relates measured in situ resistance and capacitance to the density and fabric of soil strata.

A further object of the present invention is to provide probe apparatus for measuring in situ the resistance and capacitance of soil.

Yet another object of the present invention is to provide a balanceable bridge closely adjacent a soil sampling probe to enable accurate measurement of resistance and capacitance of a soil sample therein.

Other objects of the invention include method and apparatus for determining friction angle, elastic modulus, secant modulus, coefficient of dynamic settlement, stress ratio required to cause liquefaction, and permeability coefficient of soils. Further, these properties can be registered automatically.

Additional objects include method and apparatus for geo-technical studies of soils under water, for earthquake study, for deposition and transport of solids in rivers, and for other soil studies.

Further objects of the invention are to enable better initial measurement of the moisture contents of foods.

Other objects, advantages and features of the invention will become apparent from the following detailed description of embodiments presented in conjunction with the accompanying drawings.

BRIEF DESCRIPTION OF THE DRAWINGS

In the drawings:

FIG. 9 is a view in side elevation and in section of another form of probe; it is taken along the line 9—9 in FIG. 10.

FIG. 10 is a top plan view of the probe of FIG. 9.

FIG. 13 is a view in side elevation and in section of yet another form of probe.

FIG. 14 is a view in section taken along the line 14—14 in FIG. 13.

FIG. 15 is a view in section taken along the line 15—15 in FIG. 13.

FIG. 16 is a graph plotting the logarithm of the formation factor F against the logarithm of the degree of saturation S, showing a series of different sands, each with a straight-line function enabling the determination of the degree of saturation of any of them once one point on the line is known and F has been determined.

DETAILED DESCRIPTION OF SOME PREFERRED EMBODIMENTS

Figure 1:
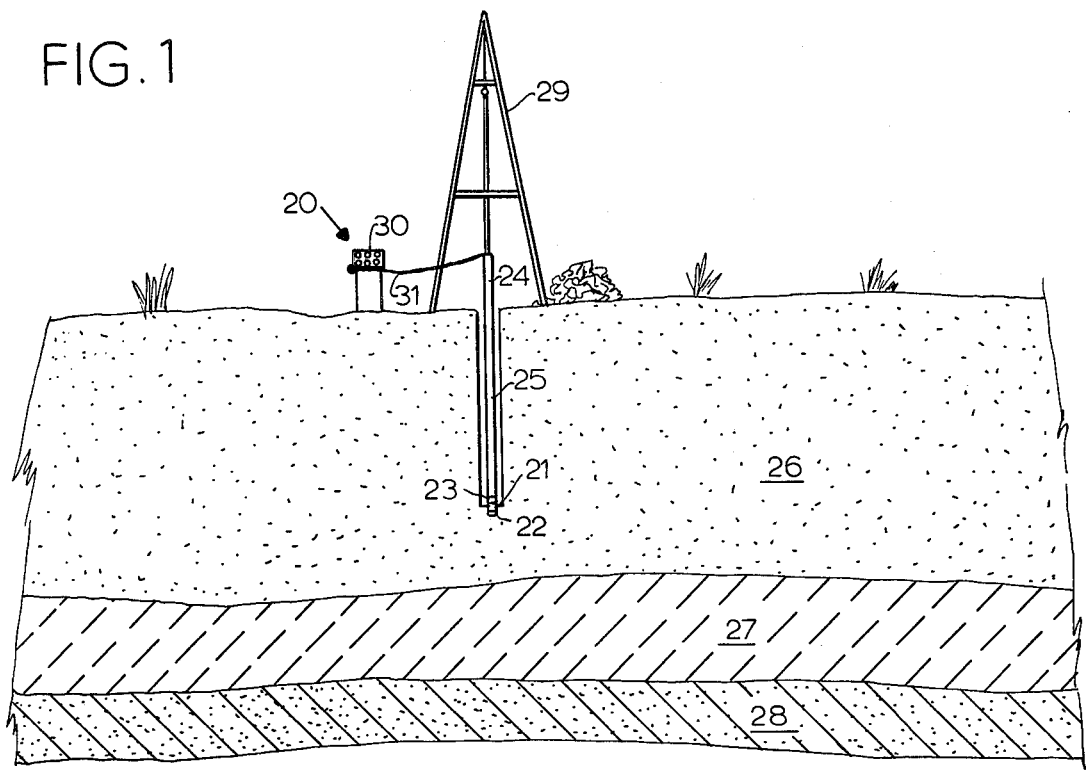
FIG. 1 is a diagrammatic view in vertical section of a soil stratum into which a sampling hole has been bored and a probe assembly embodying the principles of the present invention emplaced. Indicator apparatus of the present invention, located above ground, is connected to the probe assembly by a cable.
Figure 2:
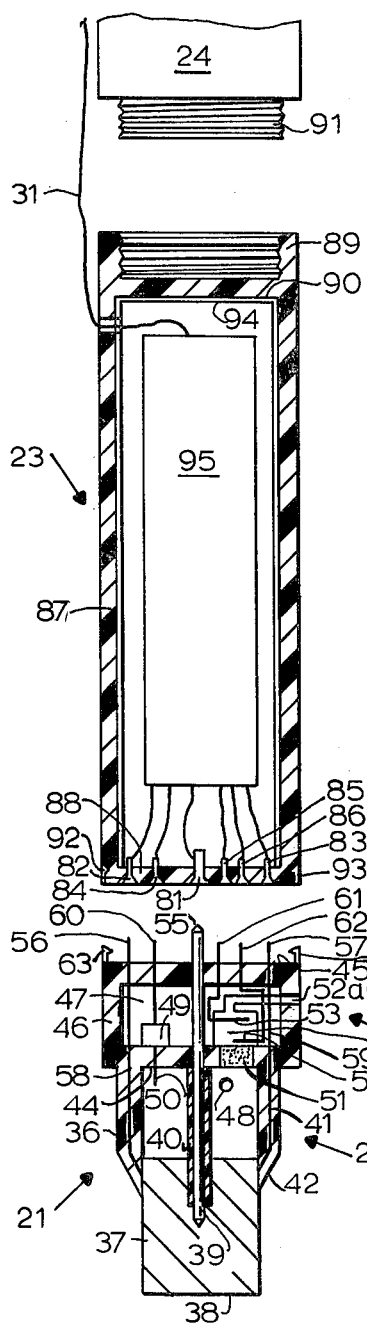
FIG. 2 is a greatly enlarged view in side elevation, section and axial separation of components comprising the probe assembly shown in FIG. 1, with some of the structure thereof broken away to reveal the interior.

Referring to FIGS. 1 and 2, apparatus 20 embodying the principles of the present invention is illustrated. In FIG. 1, the apparatus is shown to include a probe assembly 21, including a sensor element 22 at the lower end and a measuring element 23 above the sensor 22. The probe 21 is at the lower end of a probe shaft 24 which is emplaced in a bore hole 25 which has been bored into a study stratum of soil 26. Below the sandy stratum 26 may be other strata such as clay 27 and bedrock 28, for example. A derrick 29 has been used in the drilling of the sample hole 25 and is shown supporting the probe shaft 24 in FIG. 1. An indicator and control unit 30 is located at the surface remote from the probe 21, and is connected to the measuring element 23 via a cable 31 which carries control and power signals to the probe 21 and returns electrical resistance and capacitance signals therefrom to the indicator unit 30.

PROBE ASSEMBLY 21, FIG. 2:

A preferred form of probe assembly 21 including one form of sensor element 22 compatibly configured for physical attachment to and use with the measuring element 23 is set forth in FIG. 2. Therein the sensor portion 22 is seen to include a cylindrical body 36 having a cylindrical outer metal electrode 37 at the lower end portion, the electrode 37 having an open end 38 at the bottom thereof. An axially aligned central electrode 39, preferably made of platinum, extends downwardly into the interior of the outer electrode 37 for some distance. Surrounding all but a lower tip portion of the axial electrode 39 is a plastic insulating tube 40. An outer plastic annular cylindrical upper portion 41 supports the lower electrode 37 which is joined thereto. The annular upper portion 41 has a tapered portion 42 at the point of joining the lower electrode 37. A housing 43, preferably made of plastic, is preferably integrally formed with the upper annular portion 41. The housing has a bottom wall 44, a top wall 45, and a cylindrical sidewall 46 enclosing a space 47 between the bottom and top walls 44 and 45.

A vent hole 48 is provided through the upper portion 41 adjacent the bottom wall 44 of the housing. The space 47 within the housing is occupied by a temperature transducer 49 having a temperature-sensitive tip 50 which extends through and for a small distance below the bottom wall 44.

The sensor element 22 can also include a pore fluid testing element 51 for measuring the characteristics of pore fluid. An opening through the bottom wall 44 is occupied by a porous stone filter 52 through which water and other pore fluid can pass, but which excludes soil. The pore fluid testing element 51 is mounted to the bottom wall 44 directly over the porous stone 52 and defines a chamber having two separated electrodes 53 and 54 therein. A small vent tube 52a enables pore fluid to enter the chamber.

A series of plugs extends through the top wall 45 in a predetermined pattern. One plug 55 constitutes an extrusion of the axial electrode 39. Two other plugs 56 and 57 are to two wires 58 and 59 respectively. The wires 58 and 59 pass through the upper portion 41 and make electrical contact with the cylindrical electrode 37 near its upper end. Another plug 60 is connected to the temperature transducer 49; and, two other plugs 61 and 62 are connected respectively to the electrodes 53 and 54 within the chamber of the pore fluid testing element 52.

Two locking projections 63 and 64 are molded integrally with, and extend upwardly from, the top wall 45 of the housing 43. The projections 63 and 64 have oppositely facing, inwardly projecting camming and locking surfaces for achieving a locking engagement with complementary structural portions of the measuring element 23 which is also provided with jacks 81, 82, 83, 84, 85, and 86 which are sized and aligned to mate with the plugs 55, 56, 57, 60, 61, and 62 respectively, so that the sensor element 22 is electrically connected to the measuring element 23 by being plugged into, and locked in axial alignment with, the measuring element 23. Many widely differing plugging and locking configurations may be used to secure the sensor element 22 to the measuring element 23, and the particular structure shown in FIG. 2 is by way of one example and is in no sense limiting.

The measuring element 23 includes an integrally molded cylindrical plastic tube 87 having a bottom 88 closing the bottom opening and a threaded flange portion 89 and top 90 closing the top opening of the tube 87. The threaded flange portion is adapted to engage a threaded lower end 91 of the probe shaft 24.

The jacks 81, 82, 83, 84, 85, and 86 are mounted through the bottom 88 of the tube 87. Recessed locking structure 92 and 93 complement the projections 63 and 64 of the sensor element 22 to effectuate a locking mechanism for holding the sensor 22 plugged into the measuring unit 23.

A metallic shield 94 is provided inside the tube 87 except at the bottom, and it may be provided even at the bottom so long as it does not short out the jacks mounted therein. An enclosed and perhaps encapsulated measuring circuit 95 is placed inside the shield 94 within the tube 87. One end of the circuit 95 is provided with wires extending and connected to the jacks 81, 82, 83, 84, 85, and 86. The control and monitoring cable 31 leads from an opposite end of the circuit 95 and is dressed through an opening in the upper region of the tube 87. Alternatively, the cable 31 could pass through an opening in the top 90 and thence upwardly through the interior of the probe shaft 24. As shown in FIG. 2, the cable 31 is dressed upwardly along the sidewall of the shaft 24 and may be held in place by tape, clips, etc.

Figure 3:
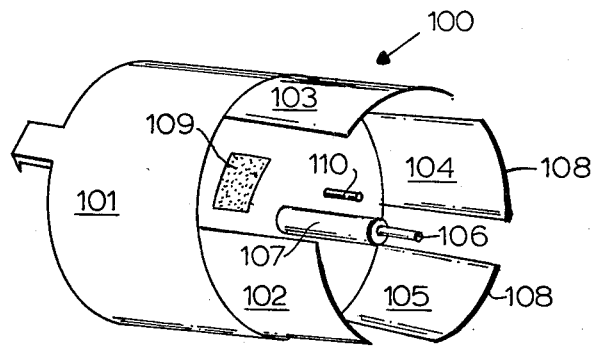
FIG. 3 is a view in perspective of another form of sensor element embodying the principles of the present invention for the probe assembly shown in FIG. 2.

SENSOR 100, FIG. 3:

An alternative sensor 100 embodying the principles of the present invention is shown in perspective view in FIG. 3. The sensor 100 includes the same electrical elements present within the sensor 22 shown in and described in connection with FIG. 2: sensor elements for a soil sample, pore fluid sensor and temperature transducer. The sensor includes plugs of the same size and arrangement as the plugs of the sensor 22, and also includes locking projections for locking it to the measuring element 23 as with the probe 22.

The sensor 100 includes a hollow, cylindrical plastic housing 101 from which four detached electrodes 102, 103, 104, and 105 extend in a cylindrical pattern. A central axial electrode 106 also extends from the housing 101 and is equidistant from the electrodes 102, 103, 104, and 105. An insulating sleeve 107 shrouds a major segment of the axial electrode 106 from the housing outward. Edges 108 of the electrodes 102, 103, 104, and 105 are sharpened into knife-like blades. The provision of four detached, yet electrically parallel, outer electrodes provides better penetration into some types of soil than the cylindrical electrode 37 of the sensor 22.

The housing 101 includes a porous stone 109 seated therein as a filter for the pore fluid sensor, and a temperature transducer tip 110 for use with the temperature transducer.

Figure 4:
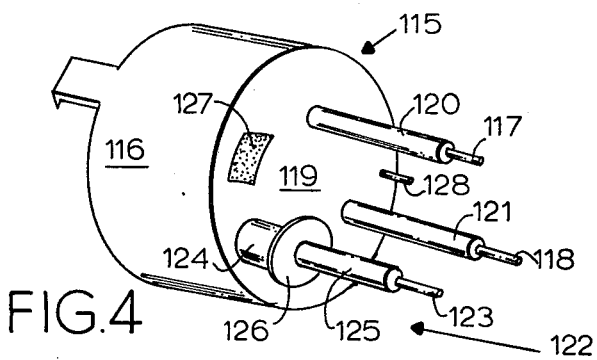
FIG. 4 is a view in perspective of yet another form of sensor element embodying the principles of the present invention, also adapted to function as a part of the probe assembly shown in FIG. 2.

SENSOR 115, FIG. 4:

Another sensor 115 embodying the principles of the present invention is shown in perspective view in FIG. 4. The sensor 115 enables bidimensional measurement of resistance and capacitance of soil samples and the like, i.e., measurements along two quite different lines of direction.

The sensor 115 has a cylindrical body 116 with ends closed and an interior compartment containing a pore fluid sensor, a temperature transducer and electrical connections, etc. Plugs and locking projections enable the sensor 115 to be securely attached to the measuring element 23 in the same manner that the sensors 22 and 100 are attached.

Two single electrodes 117 and 118 project from a bottom wall 110 of the housing 116. The electrodes are preferably of platinum or stainless steel and are shrouded for most of their length with insulating sleeves 120 and 121. The electrodes 117 and 118 enable sensing and measurement of capacitance and resistance of a soil sample along a line of direction running therebetween.

A dual electrode 122 projects from the bottom wall 119 a spaced distance from the electrodes 117 and 118. The electrode 122 includes two coaxial conductors, a central conductor 123 and an outer electrode 124. An insulating sleeve 125 separates the central and outer conductors 123 and 124, holds them in relative fixed position and extends over most of the length of the dual electrode 122, leaving only a small end portion of the central conductor 123 exposed. A flange 126 is placed over the sleeve 125 and joined to the end of the outer conductor 124. The exposed portion of the central conductor 123 and the flange 126 enable sensing and measurement of capacitance and resistance of the soil sample along a line of direction extending between the conductor 123 and the flange 126, a direction approximately normal to the line of direction between the electrodes 117 and 118.

As with the other sensors 22 and 100 already described, the bottom wall 119 of the sensor 115 has a porous stone 127 seated therein for use as a filter for a pore fluid sensor mounted directly therebehind. Also, a sensing tip 128 of a temperature transducer extends from the bottom wall 119.

Figure 5:
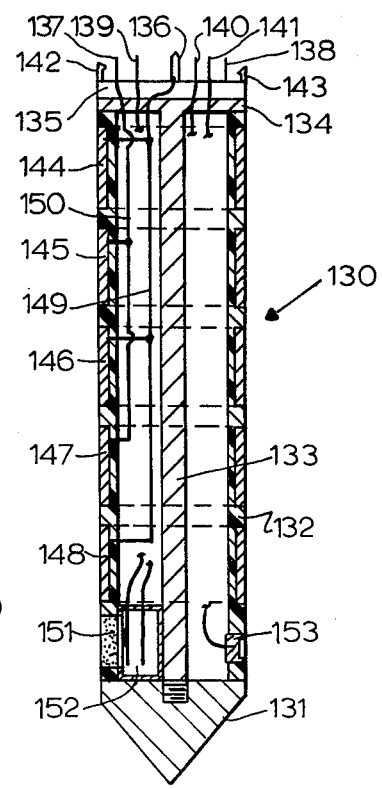
FIG. 5 is a view in side elevation and section of a further form of sensor element embodying the principles of the present invention, being adapted for use as part of the probe assembly shown in FIG. 2.

SENSOR 130, FIG. 5:

A sensor 130 of somewhat more rugged design than the already described sensors 22, 100, and 115 is illustrated in the view in elevation and section of FIG. 5. The sensor 130 includes an end-pointed hard metal cylindrical tip 131, preferably of tempered steel. A plastic cylinder 132 of the same outside diameter as the tip 131 is seated on the tip and extends upwardly therefrom. The cylinder 132 is locked to the tip 131 by a special bolt 133 having a top flange 134 which fits over the cylinder 132, and a threaded end 135 which mates with a threaded recess in the tip 131 along its axis.

Securely mounted to the top of the top flange 134 is a plastic plug 135 which is fitted with electrical plug contacts 136, 137, 138, 139, 140, and 141 which are of the same size and arrangement as those of the other sensors 22, 100, and 115 so that the sensor 130 may be interchanged therewith. Insulated openings are provided through the top flange 134 for connecting wires between the contacts of the plug 135 and sensing elements of the sensor 130. The plug 135 is, of course, provided with locking projections 142 and 143 for engagement with the recesses 92 and 93 of the measuring element 23, shown in FIG. 2.

Surrounding the outside of the plastic cylinder 132 and recessed to be flush therewith are five metallic bands 144, 145, 146, 147, and 148. The bands 144, 145, 146, 147, and 148 are spaced apart and electrically insulated from each other. Three of the bands 144, 146, and 148 are connected in parallel by a wire 149 which is connected to the contact 136 of the plug 135. The two intermediate bands 145 and 147 are connected in parallel by a wire 150 to the contact 137.

A porous stone filter 151 is seated in an opening of the plastic cylinder. Behind the filter 151 is a pore fluid sensor 152 having an interior chamber with two electrodes therein which are connected by wires to the contacts 140 and 141 of the plug 135. A temperature transducer 153 is also mounted in a suitable opening through the plastic side wall. An electrical connection from the transducer extends to the contact 139 of the plug 135.

Figure 6:
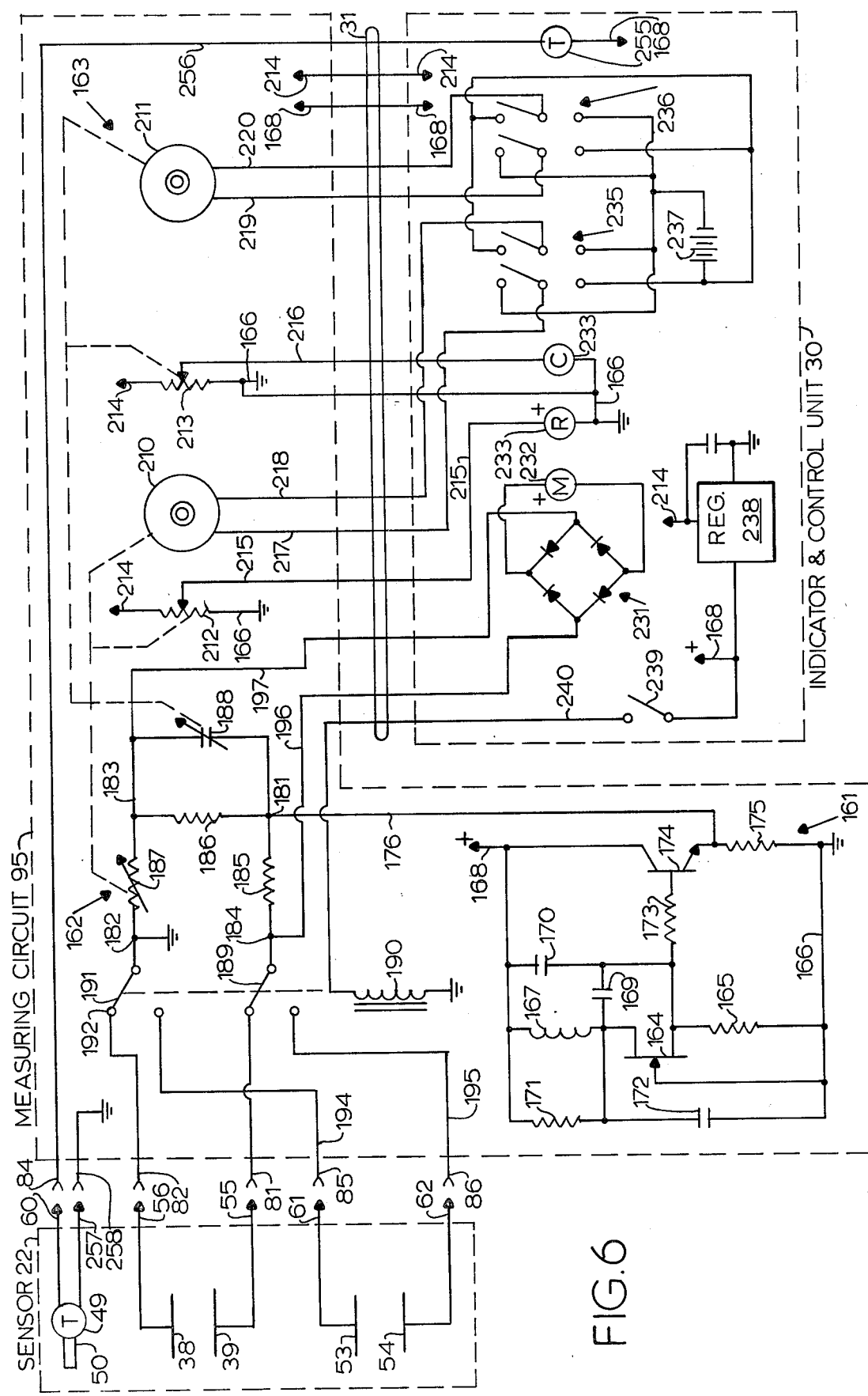
FIG. 6 is a schematic circuit diagram of one form of apparatus embodying the principles of the present invention shown in FIG. 1.

ELECTRICAL CIRCUITRY, FIG. 6:

The apparatus 20 is shown electrically in the schematic diagram of FIG. 6. Therein, the probe unit 21 is divided into its three major subsections: the sensor 22, the measuring circuit 95, and the indicator and control unit 30.

In turn, the measuring circuit 95 has three subsections: an R-F oscillator section 161, a capacitance bridge section 162, and a remote control section 163.

The oscillator 161 includes a junction field effect transistor 164 having a source resistor 165 to ground 166. The gate of the JFET transistor 164 is also directly connected to ground 166. An inductor 167 connects from the drain of the transistor 54 to a plus supply bus 168. A tank-circuit capacitor 169 is connected from the source to the drain of the transistor 164. The source is also connected to the plus supply bus 168 by another tank capacitor 170, the capacitors 169 and 170 forming a pi-network with the inductor 57. The drain of the transistor 164 is connected to the plus supply bus 168 by a resistor 171, and to ground by a capacitor 172.

Output from the oscillator 164 (a radio-frequency current, preferably about one megaHertz and at least one-half megaHertz) is taken from the source thereof through a resistor 173 to the base of an emitter-follower buffer transistor 174. The collector of the transistor 174 is connected directly to the plus supply bus 168, and the emitter thereof is connected to ground 166 through a load resistor 175. Output from the buffer 174 is taken from the emitter via a line 176 to the bridge section 162.

The bridge circuit 162 includes input nodes 181 and 182, with the node 181 being connected to the oscillator system output line 176, and the node 182 being connected directly to ground 166. Output nodes 183 and 184 are provided between the input nodes 181 and 182. A fixed value resistor 185 is connected between the nodes 181 and 184, and a fixed value resistor 186 (identical in value to the resistance of the resistor 185) is connected between the nodes 181 and 183. A variable resistor 187 is connected from the node 182 to the node 183. A variable capacitor 188 is connected from the node 181 to the node 183.

The node 184 is connected, for example, to one moving contact 189 of a double pole double throw relay 190. Similarly, the node 182 is connected to the other moving contact 191 of the relay 190. Two alternative fixed contacts 192 and 193 associated with the moving contact 191 are connected to two jacks, e.g., 82 and 85, while two complementary alternative fixed contacts 194 and 195 associated with the moving contact 189 are connected to two other jacks 81 and 86. In this way, the bridge section 162 may be switched by activation of the relay 190 between the soil sample sensor elements 38 and 39 and the pore fluid sensor elements 53 and 54. Electrical output from the bridge 162 is taken from the nodes 184 via a line 196, and from the node 183 via a line 197, the lines 196 and 197 extending to the indicator and control unit 30 within the cable 31.

The remote control section 163 includes a servomotor 210 which is mechanically linked to operate the potentiometer 187. A servomotor 211 is similarly mechanically linked to operate the variable capacitor 188. A resistance indicator potentiometer 212 is controlled by the resistor servomotor 210, and a capacitance indicator potentiometer 213 is likewise linked mechanically to the capacitor servomotor 211. One end of each of the potentiometers 212 and 213 is connected to ground 166 and the other end of each is connected to a regulated supply bus 214. A resistance value line 215 extends from the wiper of the potentiometer 212 to the indicator and control unit 30 within the cable 31. Similarly, a capacitance value line 216 is connected from the wiper of the potentiometer 213 and extends to the indicator and control unit 30 as a part of the cable 31. Two control lines 217 and 218 from the control unit 30 provide power to the servomotor 210 and two control lines 219 and 220 provide power to the servomotor 211 from the indicator unit 30.

Figure 7:
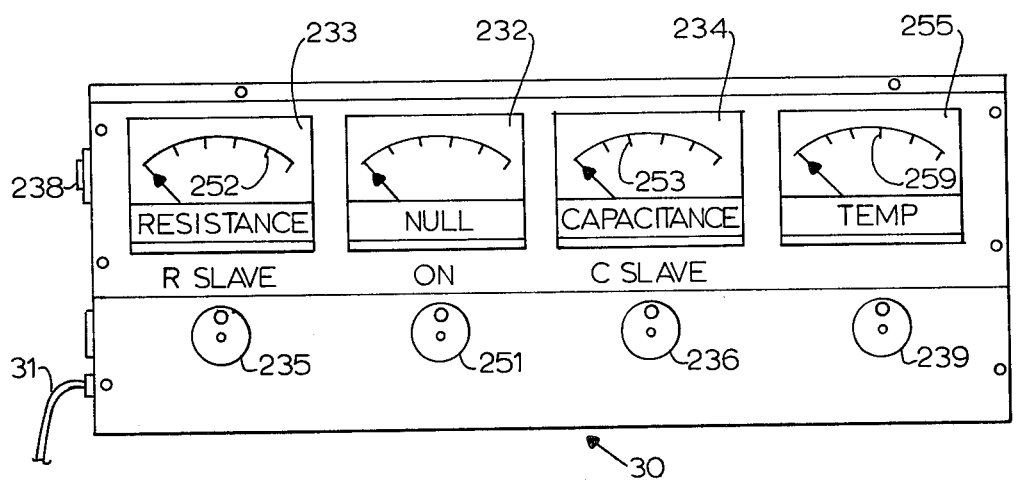
FIG. 7 is a greatly enlarged view in front elevation of the indicator apparatus shown in FIG. 1.

The indicator and control unit 30 is shown schematically in FIG. 6, and physically in FIG. 7. It includes a full wave diode rectifier bridge 231, preferably comprising germanium diodes. The alternating-current nodes of the rectifier 231 are connected to the bridge output lines 196 and 197, and the direct-current nodes of the rectifier 101 are connected to a sensitive microammeter null meter 232. A voltmeter meter 233, calibrated to indicate resistance directly, is connected between the resistance value line 215 and ground 166. A voltmeter meter 234, calibrated to indicate capacitance directly, is connected to the capacitance value line 216 and to ground 166. A double pole, double throw switch 235 has its switching contacts connected to the lines 217 and 218 and provides reversible polarity direct current to operate the resistor control servomotor 210 in two opposite rotations in accordance with the position of the switch 235. Similarly, a switch 236 has its moving contacts connected to the lines 219 and 220 and its fixed contacts connected to supply reversible polarity direct current to the capacitor control servomotor 211. A power source 237, which may be a storage battery, is connected to the fixed contacts of the switches 235, 236 to provide the direct current in accordance with the configuration shown in FIG. 6. A solid-state integrated circuit regulator 238 is connected between the plus supply bus 168 and ground 166 and provides regulated voltage to the regulated voltage supply bus 214.

A single pole, single throw switch 239 is connected between the plus supply bus 168 and a line 240 to the armature of the relay 190, the other end of the armature thereof being grounded. The switch 239 in the control unit 30 activates the relay to switch the bridge circuit 162 between the soil sample sensing elements 38, 39 and the pore fluid sensing elements 53, 54 of the sensor 22, FIG. 2.

A direct reading temperature motor 255 is provided in the indicator and control unit 30. The meter 255 is connected between the plus supply bus 168 and a line 256 leading to the temperature transducer 49 in the probe sensor 22 via the jack 84 and the mating plug 60. The transducer 49 is provided with a return connection to ground via a plug 257 and a mating jack 258 (not shown in FIG. 2).

As seen in FIG. 7, the indicator and control unit 30 may be provided in a suitable housing 250 that includes an on-off switch 251 in addition to the relay switch 239 resistor control switch 235, capacitor control switch 236, and the four indicators: the null meter 232, the resistance meter 233, the capacitance meter 234 and the temperature meter 255. The solid-state regulator chip 238 is mounted on the side of the case 250. The cable 31 extends from the case 250 to the measuring element 95 of the probe 21, as shown in FIGS. 1 and 2. The resistance meter 233, the capacitance meter 234, and the temperature meter 255 are calibrated so that resistance and temperature capacitance values may be read directly from their scales 252, 253, and 259, respectively.

ELECTRICAL CIRCUIT OF FIG. 8

Figure 8:
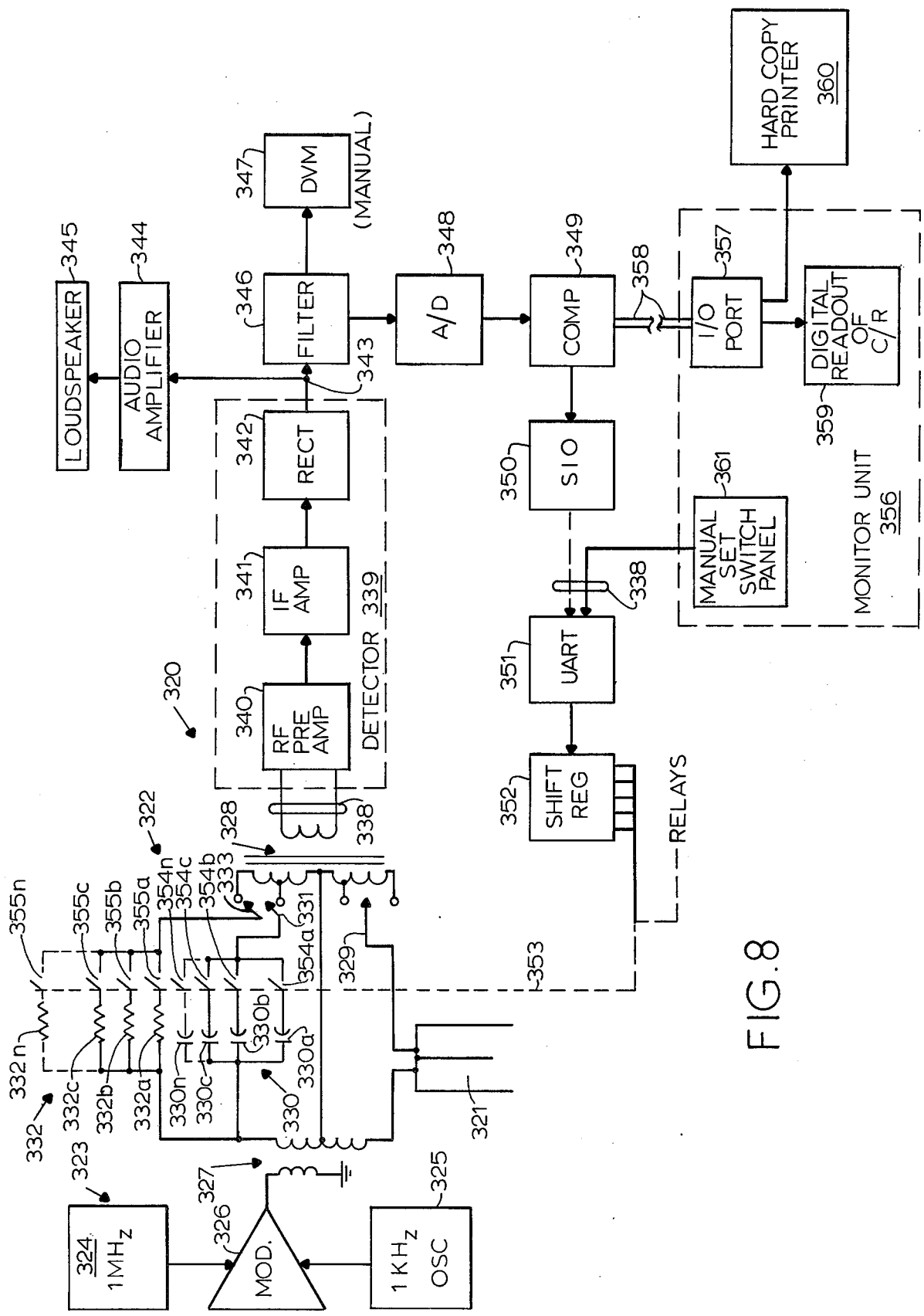
FIG. 8 is a schematic circuit diagram of another form of apparatus embodying the principles of the present invention which enables an operator to select between automatic and manual measurement of soil sample phenomena.

FIG. 8 sets forth an embodiment of soil measurement apparatus constructed in accordance with the present invention which may be operated manually or automatically. Therein a probe 320 includes a sensor 321 which may be similar to the sensors 22, 100, 115, and 130 shown in FIGS. 2, 3, 4, and 5, and described in connection therewith. The pore fluid sampling element 52 and related switching circuit is not shown in connection with the probe 320 for the sake of clarity. In practice they would probably be included.

The probe 320 includes a bridge circuit 322 and an oscillator section 323. The oscillator includes an R-F oscillator 324, preferably operating at about one megaHertz, and an audio oscillator 325 operating preferably at about one kiloHertz. The oscillators 324 and 325 are connected to a modulator stage 326 whereupon the audio signal from the oscillator 325 is modulated on the R-F carrier generated by the oscillator 324. The output from the modulator stage 326 is connected to a primary winding of a transformer 327 having a center tapped secondary winding within the bridge circuit.

The bridge circuit includes another transformer 328 having a multiply-tapped and center-tapped primary winding, with the center tap thereof being connected directly to the center tap of the secondary of the transformer 327. One segment of the centertapped secondary of the transformer 327 is connected to one of the electrodes of the sensor 321, and one segment of the primary winding of the coil 328 is connected to the other electrode of the probe sensor 321 through a tap selection switch 329 which may be used to vary the transformation ratio of the transformer 328. The tap selection switch enables the large range of resistance values desired to be measured with the help of a much smaller range of standards.

An incrementally variable capacitance network 330 is connected from the other end of the secondary of the transformer 327 to the other end of the primary of the transformer 328 through a tap selection switch 331. The network 330 includes capacitors 330a, 330b, 330c . . . 330n, to provide the incremental variation of capacitance to balance the bridge circuit 322. In like manner, an incrementally variable resistance network 332 is connected to the secondary of the transformer 328 through a tap selection switch 333. The resistance network includes the resistors 332a, 332b, 332c . . . 332n.

The off-null radio-frequency error signal from the bridge circuit 322 in the probe 320 is taken from the secondary winding of the transformer 328 via a cable 338 to a detector 339 which includes an R-F preamplifier 340, where an amplitude-modulated radio-frequency carrier is amplified to a suitable predetermined level. Thereupon the signal is provided to an intermediate-frequency amplifier circuit 341 for further amplification. The output of the amplifier 341 is passed through a rectifier 342 to separate the audio modulating signal from the carrier. An output line 343 from the rectifier 342 may be connected to an audio amplifier 344 driving a loudspeaker 345 or any other indicating device which is useful for indicating aurally the null point of the bridge 322. The output line 343 may also be connected to a filter 346 to provide a filtered analog DC voltage. The analog voltage may be sent to a direct reading digital voltmeter 347, and to the input of an analog to digital converter 348 wherein the magnitude of the analog voltage is digitized. The digitized output of the analog to digital converter 348 is provided as an input to a digital computer 349. The computer 349 is preferably implemented as a dedicated special purpose microcomputer such as the Intersil IM6100 and including an operating system and data base in programmed read only memory and a scratchpad random access memory.

The computer 349 processes the input digital signal from the analog to digital circuit 348 and determines automatically the incremental change required in the capacitance network 330 and the resistance network 332 to bring the bridge 322 into balance, when a soil sample is emplaced in the sensor element 321. The incremental change in capacitance and resistance is sent to the probe 320 through a serial input/output port 350 via conductors in the cable 338 to a universal asynchronous receiver transmitter 351 in the probe 320 which loads the serial signal into a shift register 352 also in the probe. The shift register 352 functions to decode the output from the computer into incremental capacitance and resistance switch signals.

Switch lines 353 from the shift register 352 are connected to switches in series with the elements of the incremental variable capacitance network 330, there being a switch 354a for the capacitor 330a, a switch 354b for the capacitor 330b, a switch 354c for the capacitor 330c, and a switch 354n for the capacitor 330n of the network 330. In like manner, others of the output lines 353 from the shift register 352 are connected to switches 355 in the incremental variable resistance network 332. Thus, a switch 355a is in series with the resistance element 332a, a switch 355b is in series with the resistance element 332b, a switch 355c is in series with the resistor 332c, and the switch 355n is in series with the resistor 332n. The switches 354 and 355 may be implemented as relays or as solid-state switching devices, with either being equally well suited to the application.

A monitor unit 356 is connected to the computer 349 through an input/output interface 357 which is connected to the computer 145 via an interconnection cable 358. The input/output buffer 357 may be connected to a digital readout 359 within the remote monitor unit 154 and to a hard copy printer 360. The computer 349 calculates the capacitance and resistance of the soil sample after the computer 349 has automatically balanced the bridge circuit 322. When the resistance and capacitance values are calculated, they are then supplied to the digital readout 359 and to the printer 360 whereupon the values may be read and utilized in accordance with the principles of the present invention.

It will be appreciated by those skilled in the art that the automatic operation of the probe 320 and its associated equipment is very rapid, and once the probe sensor 321 is provided with a sample of granular soil, the computer 349 very rapidly balances the bridge 322, and provides a readout of capacitance and resistance values at the monitor unit 154.

The automatic circuitry embodiment of the present inveniton described in connection with FIG. 8, may be operated in a manual mode. For manual operation, a manual set switch panel 361 is provided in the monitor unit 356. The switch panel is connected to the UART 351 in the probe through the cable 358 and overrides the computer 349. In this way, increments of resistance and capacitance in the networks 330 and 332 of the bridge 322 may be set by setting switches in the manual set switch panel. The null point of the bridge, when undergoing manual balancing, is indicated aurally by the loudspeaker 345 and visually by the digital voltmeter 347. It is to be appreciated that the null point will occur at the point of minimum sound and meter reading.

The electrical apparatus at the surface, namely, the detector 339, amplifier 344, loudspeaker 345, digital voltmeter 347, analog to digital converter 348, computer 349, serial input/output 350, and monitor unit 356 are preferably contained in a hermietically sealed container providing capacitively activated (proximity) switches so that blowing sand at the measurement site will not enter the apparatus. Similar precautions would undoubtedly have to be taken to protect the hard copy printer 360. Alternatively, the apparatus could include sealed recording units in connection with the in/out portion 357. The recording units could then be taken to a controlled environment and read into a printer or readout thereby providing, albeit somewhat delayed, direct measurement in the site of soil phenomena.

ELECTRICAL CIRCUIT OF FIG. 12

Figure 12:
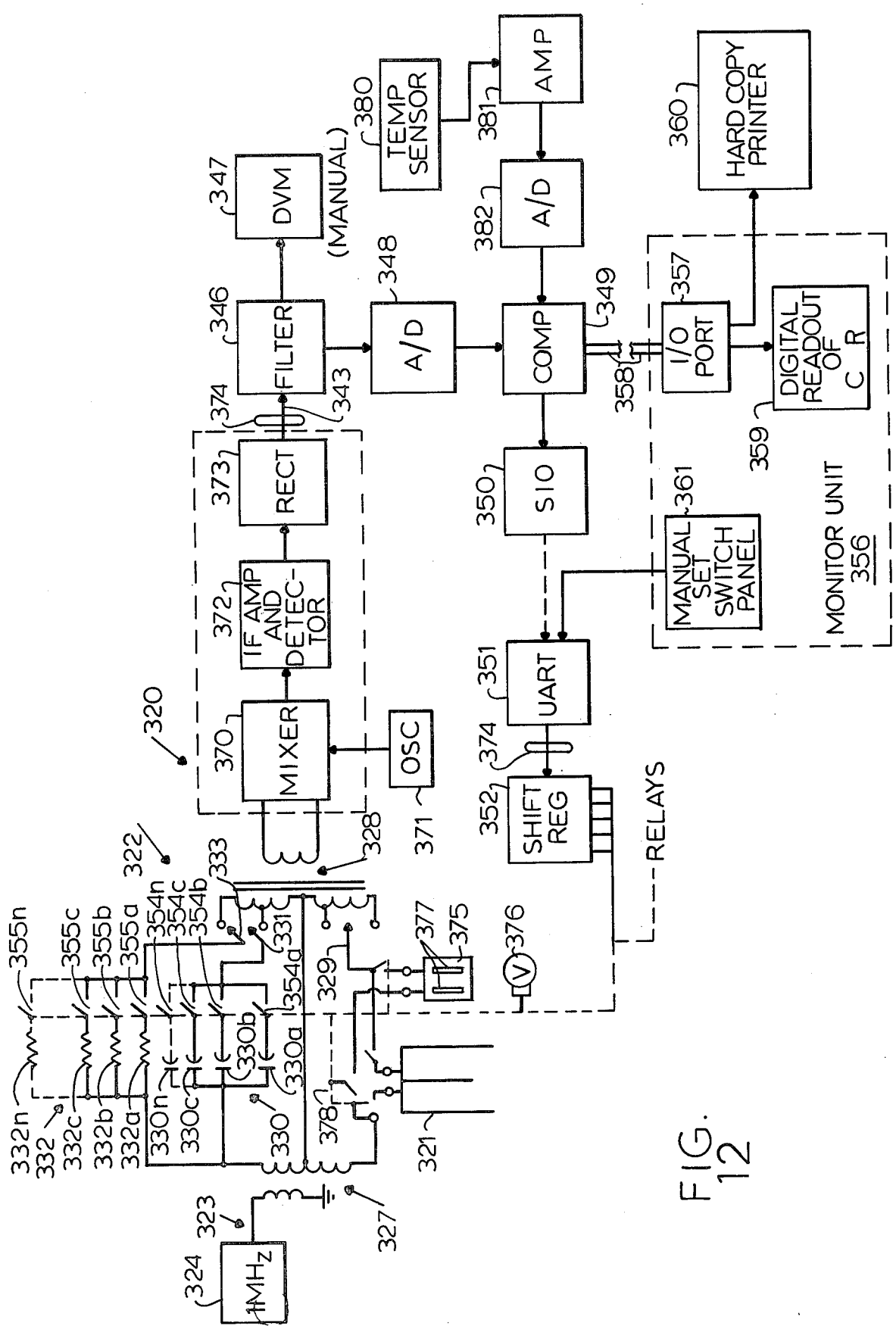
FIG. 12 is a schematic circuit diagram generally similar to that of FIG. 8 but showing a modified scheme.

FIG. 12 shows a circuit generally like that of FIG. 8 but with some significant changes. Like the circuit of FIG. 8, it employs an R-F oscillator 324, which preferably generates a frequency of about one megaHertz, since radio frequencies, i.e., frequencies of at least about one-half megaHertz, are essential for obtaining steady and reliable capacitance values from soils. However, in the FIG. 12 modification there is no modulation of the R-F signal, and that signal is fed directly to the primary coil of the first transformer 327.

The output from the secondary coil of the second transformer 328 is fed to a mixer 370, which also receives a mixing signal from an oscillator 371. This mixing signal can range in frequency from about 500 kHz to about 950 kHz. The mixer 370 is a standard type of mixer for producing a different signal having a frequency equal to the differences in frequency between the R-F signal and the mixing signal; the mixer 370, for example, may be a multiplier or a balanced modulator. For example, if the R-F signal has a frequency of 1 mHz and the mixing signal has a frequency of 900 kHz, the difference signal would have a frequency of 100 kHz.

This difference signal is then applied to an amplifier-detector circuit 372 which, preferably, first amplifies the difference signal and then detects it, so that the other signals emitted from the mixer 370 are removed. Standard I-F amplifier circuits and standard I-F detection circuitry may be used.

The detected and amplified difference signal is then rectified, as by a standard rectifier 373. All of the elements 370 through 373 may be inside the housing for the probe 320 or may be (less conveniently) located outside and above ground. If located inside the probe housing, the output from the rectifier 373 may be connected by a cable 374 to the filter 346. The filter 346 and the other elements having the same reference numerals as those in FIG. 8 may be as described in connection with that figure.

The probe 321 includes a pair of electrodes for sensing along a horizontal direction and a pair of electrodes for sensing along a vertical direction (one electrode of each pair may be the same member), and also includes a pore-liquid sensing chamber 375 having a solenoid valve 376 for admitting pore-liquid thereinto and activated by the computer 349. Electrodes 377 are put into the sensing circuitry by switches 378 by the shift register 352 (or the relays). Thus the computer 349 receives signals conveying the magnitude of the (1) horizontal resistances of the soil, (2) the vertical resistance of the soil, (3) the horizontal capacitance of the soil, (4) the vertical capacitance of the soil, (5) the pore-liquid resistance, and (6) the pore-liquid capacitance. The computer 349 also receives a temperature signal generated by a temperature sensor 380 via an amplifier 381 and an analog-to-digital converter 382. The computer 349 is preferably programmed to accommodate all these parameters.

Thus FIG. 12 shows another way of preparing the R-F signal for reception by the computer or for manual use, if desired. In both FIG. 8 and FIG. 12 the R-F signal from the bridge is converted into an amplified signal, preferably rectified, of a type suitable for feeding to a digital computer.

OPERATION OF THE SYSTEMS 20, 120

While the manually operable apparatus 20 differs somewhat structurally from automatically operated probe 320, the measurements resulting from both devices are identical. Measurements may differ slightly depending on the configuration of the sensor element and depending upon the direction of the line of measurement effectuated by the particular sensor.

The steps to be followed for measuring resistance and capacitance of granular soil in situ are first to provide access to the soil sample locus, e.g., by drilling to a fixed depth. The drill is then withdrawn and the probe may then be attached to the tip of a drill and lowered into the bore hold until a soil sample fills, e.g., the sensor 22. Thereupon, the bridge circuit is balanced, and the capacitance and resistance of the soil is directly indicated and recorded. The measured resistance and capacitance values are thereupon converted to conductivity and dielectric constant by readings from suitable calibration charts.

A small quantity, 100 grams, for example, of the measured soil sample, as well as a small quantity, 100 cc, for example, of pore fluid may be extracted from the bore hole, the sample being retained in the sensor 22 as it is withdrawn and the pore fluid being collected and withdrawn after removal of the probe. The probe may then be used to measure the conductivity of the collected pore fluid. Alternatively, the sensor 22 may be provided with the pore fluid sensor 52 and conductivity of the pore fluid may then be measured with the probe in situ. In any event, collection and measurement of the conductivity of the pore fluid is required to calculate the formation factor by using the expression:

$$F = \frac{\text{conductivity of pore fluid}}{\text{conductivity of sand-solution}} \quad (7)$$

and then applying the result in the equation for porosity, equation (4), above.

The soil sample and the pore fluid may also be subjected to laboratory analysis to confirm the accuracy and calibration of the apparatus of the present invention, if such need be the case.

If the soil is 100% saturated with pore liquid, the conductivity of the mixture of sand and liquid will, of course, be different from that of the same soil at a lower degree of saturation. However, by measuring the conductivity of the soil sample at 100% saturation, F can be determined for that condition. Then, as shown in FIG. 16, with the one point F at 100% saturation known, the characteristics of the soil in this particular are determined, for the relationship between the logarithm of the formation factor (log. F) and the logarithm of the degree of saturation (log. S) is a straight line function $f_1$ with a known slope for all sands and soils. Hence, once the point log. F at 100% S is known one can determine the degree of saturation for any in situ measurement from the reading F, for the logarithm of that F reading will intersect the curve $f_1$ at the degree of saturation. In the graph of FIG. 16, $f_2$ and $f_3$ indicate other sands with different characteristics, and they show that the slope remains the same.

With the porosity and formation factor values calculated from the in situ measurements, other engineering properties may then be derived, as follows:

(1) Friction angle
$$\phi = -148\sqrt{n/F} + 84 \qquad (8)$$

or $$\phi = 13.8F - 20.7$$

The range of expected values of friction angle is $$\phi = 25 - 55$$

(2) Coefficient of dynamic settlement:

$$c_d = -10F + 50 \qquad (9)$$

Expected values for this coefficient are 1 to 14.

(3) Stress ratio required to cause liquefaction:

$$t/\sigma_o = -1.64\sqrt{n/F} + 0.727 \qquad (10)$$

Values of $t/\sigma_o$ expected to be 0.1 to 1.

(4) Permeability coefficient K cm/sec $$K = 1.5\sqrt{n/F} - 0.18 \qquad (11)$$

The range for K would be expected to be $10^{-1}$ to $10^{-6}$ cm/sec for clay to 5 megaHertz.

Several tests have been carried out in a large box of sand using equipment described herein. The results obtained were within 1 to 2% of the actual values of porosity as well as formation factor as measured by standard laboratory equipment. Calculation of elastic modulus and secant modulus may also be accomplished with the method and apparatus of the present invention.

The method and apparatus described herein may be applied effectively to all geotechnical engineering problems dealing with sands and silts. Determination of properties of marine deposits at the bottom of the ocean, determination of the behavior of soils during earthquakes, and continuous monitoring of properties of soils before, during, and after earthquakes and otherwise, are but a few examples of the many applications to which the methods and apparatus of the present invention may be effectively applied. In addition the methods and apparatus of the present invention may be applied to determine physical properties of a wide variety of materials such as foodstuffs and other granulated, powdered, and paste materials and substances.

ANOTHER PROBE 400 (FIGS. 9 AND 10)

FIGS. 9 and 10 show another probe 400, for use in taking readings in two mutually perpendicular directions. It may be used with the circuits as described above.

A disc 401 of insulating material (e.g., Plexiglass) is secured by screws 402 to a tube 403 of metal such as brass or stainless steel, which extends both above and below the disc 401. The disc 401 is provided with two diametrically opposite receptacles 404 and 405 in which are seated, respectively, two conductive metal rods 406 and 407 (preferably brass or stainless steel, which are secured to the disc 401 by respective screws 408 and 409. The rods 406 and 407 extend down from the disc and beyond the lower edge 410 of the tube 403, to which they are clamped by clamps 411 and 412.

Each rod 406, 407 is covered by insulator tubing 413, 414, preferably of shrink tubing shrunk snugly around the rod. A conductive wire 415 passes through the disc 401 and passes down the outside of the tubing 413, and a second insulator tube 416 is shrunk onto the rod 406 and covers and protects the wire 415, which is insulated from the rod 406 by the tubing 413.

The bottom surface of the rods 406 and 407 are each covered with an insulating disc 417 and 418, respectively, which meets the shrink tubing 413, 416, and 414, respectively, to enclose and insulate the lower end of the rods 406 and 407. A tubular metal electrode 420 (e.g., brass or stainless steel) lies just below the disc 417 and is brazed to the wire 415, which may be of copper.

Two elongated rod electrodes 421 and 422 have respective pointed lower ends 423, 424 and threaded upper ends 425 and 426, which are threaded into the rods 406 and 407. To get maximum distances between the electrode 421 and 422, the tops in the rods 406 and 407 for the rods 421 and 422 may be eccentric, outwardly, as shown. The electrodes 421 and 422 each have an insulated covering 427, 428, which encircles most of this shank and also insulates them from the electrode 420. Thus, there is a possibility of sending current across a lower end of the two rod electrodes 421 and 422 and also of sending current across the electrode 420 and the lower end of the electrode 421.

The upper end of the disc 401 is attached to an adapter 430, as by screws 431. The adapter 431 has a terminal 432 for the rod 406 and electrode 421, a terminal 433 for the rod 407 and electrode 422, and a terminal 434 for the wire 415 and its electrode 420.

A passage 435 through the disc 401 has a receptacle 436 for a porous stone 437 and leads to a chamber 440 which may be provided by a separate cylinder 440a in the adapter 430, where there are terminals 441 and 442 for sending current across the liquid that passes from the soil through the stem 437 into the chamber 440. A second porous stone 443, mounted in the adapter 430 and joined by a passage 444 to the chamber 440, provides for the exit of air from the chamber 440.

A temperature probe 445 is also provided.

The adapter 430 has a series of output terminals 446, 447, 448, 449, 450, and 451 which are connected internally to the terminals 432, 433, 434, 441, 442, and temperature probe 445.

The operation is substantially the same as for the sensor 115.

THE PROBE 500 OF FIGS. 13–15

The probe 500 is, in many ways like the probe 400, but it is more rugged and has several advantages that will be pointed out in the following description. Two conductive metal rods 501 and 502 have respective lower tapered portions 503 and 504 and end, respectively, in smaller-diameter electrode portions 505 and 506 with pointed ends 507 and 508.

The upper portions of the rods 501 and 502 are braced by a large insulating cylindrical body 510 through passages 511 and 512 they pass. The lower end portion 513 of the body 510 is tapered, as by two sloping sides 514 and 515 (FIG. 14), to assist in driving the probe 500 into place for a measurement. Below the body's lower end 516, the rods 501 and 502 are braced by an intermediate relatively thin, flat insulating member 517. This member 517 helps to maintain the proper spacing between the rods 501 and 502 (and therefore between the electrodes 505 and 506) but, being thin, does not interfere with (and in fact may assist) the operation of driving the electrodes 505 and 506 into their measuring position. The insulating member 517 may be joined to the lower end 516 of the body 510 by an insulating gasket 518 and there may be an insulating rim 519 at its lower end.

Below the body 510 the rods 501 and 502 are surrounded by tubular insulators 521 and 522, respectively.

The electrodes 505 and 506 are used to make resistance and capacitance measurements in the horizontal direction. An electrode 523 is used with the electrode 505 to make measurements in the vertical direction. The electrode 523 encircles the insulating tube 521, which insulates it from the rod 503, while an insulated lead 524 extends up inside a recess 525 in the member 517 and through a passage 526 in the body 510 to the upper end thereof.

Another advantage of the probe 500 is its ability to secure pore liquid from a locus closely adjacent to the electrodes 505 and 506. For this purpose, the member 517 is provided with an interior bore or passage 527 leading from near its lower end up to the upper end, where it joins a passage 528 in the body 510. A suitable filter 529 (porous stone or replaceable cotton padding, for example) may be provided in the passage 527 or in the inlet openings 530 at or near the lower end of the passage 527. The openings 530 preferably comprise a transverse bore.

Another feature is that the pore-liquid passage 528 in the body 510 leads up to a solenoid-actuated valve 531, which is normally closed. When the valve 531 is actuated (as by a manual switch above ground or by an automatically or event-activated switch, the pore liquid can pass from the passage 528 into a conduit 532 that conducts it into a pore-liquid chamber 533. The valve 531 enables the operator to restrain the passage of pore liquid into the chamber 533 until a desired amount is in the conduit 527 and also enables a cut-off once the chamber 533 is filled to a desired level. The chamber 533 contains electrodes 534 and 535 for determining pore-liquid conductivity. Gas may be vented, but FIGS. 13 and 14 show an expandable enclosure 536, like a balloon, into which the gas flows from the chamber 533. Hence, no venting to atmosphere is necessary.

A temperature probe 537 and lead 538 are also provided. Preferably the temperature probe 537 is located near the lower edge of the member 517.

Connections for the various leads may be as before, and the circuit of FIGS. 6, 8, or 12 may be used.

FURTHER FEATURES AND APPLICATIONS OF THE INVENTION

For the first time, this invention relates the electrical properties of soils to their mechanical properties. Some of these relationships have already been pointed out, and others will be discussed. From in situ measurements alone of the electrical properties, the mechanical properties can be calculated and instantaneously printed out on a screen or chart.

For clays, one can extend the method by using different frequencies to measure the resistance and capacitance at, for example, 1 megaHertz, then at 5, 10, 50, and 100 megaHertz and from these measurements predict the mechanical properties and also the type of clay and the amount in a particular such surface layer.

Whereas heretofore the in situ density had been considered the major factor affecting the mechanical behavior of soils, it is now apparent that the structure of soils is the major factor controlling the mechanical behavior. The structure of soil includes three aspects: (1) the spatial arrangement of the solid particles, (2) the shape, size, and size distribution of the solid particles, and (3) the associated void. However, none of the methods heretofore in use could predict even the in situ density and had to rely on combinations of laboratory and field instruments.

The present invention can measure the in situ density directly. It can also evaluate the soil-structure aspects and can thereby provide a "packing index" of the soil. It can also give a direct reading of relative density. Such a characterization makes it possible to predict the liquefaction behavior of soils.

1. DETERMINATION OF IN SITU DENSITY FROM FIELD MEASUREMENTS ALONE

An expression developed by Rayleigh can be extended to determine in situ porosity of uniformly graded sands.

$$\frac{1 - 1/F}{1 + 1/F} = (1 - n) \qquad (12)$$

where n is the porosity and F is the "formation factor" defined by $$F = \frac{\text{conductivity of pore fluid}}{\text{conductivity of (soil + solution)}} \qquad (7)$$

The formation factor F is a directional structure index parameter which depends on particle shape, particle gradation, particle orientation, and the associated voids.

By conventional algebraic manipulation and solving for n, the above expression becomes $$n = (2/1+F) \qquad (13)$$

and the validity of the expression has been tested by measurement on three different sands.

| Type of Sand | Porosity | F Measured | Predicted Porosity |
|---|---|---|---|
| Monterey 'O' | .410 | 3.90 | .410 |
| Ottawa C109 | .400 | 3.86 | .410 |
| | .385 | 4.1 | .390 |
| | .375 | 4.28 | .380 |
| | .38 | 4.22 | .380 |
| Sierra Diamond | .44 | 3.7 | .43 |

The above results show that porosity can be predicted in the field from direct measurements without resorting to calibration of the sand in the laboratory.

2. DETERMINATION OF RELATIVE DENSITY IN THE FIELD

Several experimental results have confirmed that, at maximum porosity, the formation factor of sands is about 3. This fact can be used to determine the relative density of uniformly graded sands. The F value at the minimum porosity for uniformly graded sands is about 4.8. This fact can be used to determine the relative density $D_r$ in the field as follows:

$$D_r = (3 - F/3 - 4.8) \qquad (14)$$

or $$D_r = (F - 3/1.8) \qquad (15)$$

3. DETERMINATION OF THE STATE OF PACKING OF SANDS

An indirect method to determine the state of packing or arrangement of sands is to define a parameter called the coefficient of anisotropy, A:

$$A = \sqrt{F_V/F_H} \quad (16)$$

where $F_V$ is the formation factor as measured between vertical electrodes (e.g., across the electrodes 420 and 421), and $F_H$ is the formation factor measured between horizontal electrodes (e.g., across the electrodes 421

$$F_V = 1 + 1 - n/n \, f_V \quad (18)$$

$$F_H = 1 + 1 - n/n \, f_H. \quad (19)$$

Furthermore, $$f_v = f_o \cos\phi + f_{90} \sin\phi \quad (20)$$

$$f_n = \tfrac{1}{2}[f_o + f_{90} + \cos^2\phi(f_{90} - f_o)] \quad (21)$$

where $\phi$ is the orientation of the major axis relative to the vertical direction of measurement and $f_o$ and $f_{90}$ are form factors where the current is, respectively, parallel to and perpendicular to the major axis.

TABLE 1: FORMATION FACTOR, SHAPE FACTOR AND ANISOTROPY INDICES FOR SANDS TESTED

| Sand/ Preparation | Porosity n | Uncorrected Box Vertical Formation Factor $F_1$ | 3-Dimensional Data Horizontal Formation Factor $F_2$ | 3-Dimensional Data Horizontal Formation Factor $F_3$ | Cylinder Vertical Formation Factor $F_V$ | Geometrical Correction Factor $\beta$ *1 | Corrected Horizontal Formation Factor $F_H$ *2 | Anisotropy Index A *3 | Average Formation Factor $\bar{F}$ *4 | Shape Factor X *5 |
|---|---|---|---|---|---|---|---|---|---|---|
| Monterey 'O' Pluviated | 0.380 | 4.05 | 3.91 | 3.93 | 4.32 | 1.067 | 4.18 | 1.016 | 4.23 | 0.98 |
| Monterey 'O' Moist Tamped | 0.397 | 3.70 | 3.76 | 3.73 | 3.92 | 1.059 | 3.97 | 0.994 | 3.95 | 0.98 |
| Monterey 'O' Moist Vibrated | 0.419 | 3.42 | 3.57 | 3.52 | 3.47 | 1.015 | 3.60 | 0.982 | 3.56 | 0.98 |
| Sierra Diamond Pluviated | 0.417 | 3.84 | 3.55 | 3.53 | 3.81 | 0.992 | 3.51 | 1.042 | 3.61 | 1.12 |
| Sierra Diamond Moist Tamped | 0.439 | 3.39 | 3.44 | 3.47 | 3.46 | 1.021 | 3.53 | 0.990 | 3.51 | 1.12 |
| Ottawa C109 Pluviated | 0.361 | 4.05 | 3.99 | 4.01 | 4.32 | 1.067 | 4.27 | 1.006 | 4.29 | 0.92 |

*1 $\beta = \dfrac{F_{V\,Cylinder}}{F_{1\,Box}}$

*2 $F_H = \beta \dfrac{F_2 + F_3 \, Box}{2}$

*3 $A = \dfrac{F_V}{F_H}$

*4 $\bar{F} = \dfrac{F_V + 2\bar{F}_H}{3}$

*5 $X = \dfrac{Fn - 1}{1 - n}$ and 422).

Different methods of sample preparation result in different particle and contact normal orientations. Samples pluviated in air tend to orient themselves with their long axis in a horizontal plane. Moist tamping tends to orient the particles with more long axes in the vertical direction. Moist vibrated samples have an even greater tendency toward vertical orientation than tamped samples. The path of electric current through sand samples is dependent on orientation of particles. It is reasonable that a current path will be tortuous in a direction perpendicular to the particle long axis orientation. For pluviated samples then, the vertical formation factor, $F_V$, should be greater than horizontal formation factor, $F_H$. This reasoning is supported by data summarized in Table 1.

The coefficient of anisotropy can be used in conjunction with other factors. Thus, defining f as a function of shape and orientation, $$F = n^{-f}, \quad (17)$$

and the formation factors $F_V$ and $F_H$ in formula (16) can be related to $f_V$ and $f_H$, as follows:

4. DETERMINATION OF THE SHAPE OF PARTICLES

This is carried out using an expression relating F and n to a shape factor, X:

$$X = F \cdot n - 1/1 - n \quad (22)$$

X has a value of 2 for spheres and is less than 2 for spheroids, X decreasing as the axial ratio of the spheroid increases.

5. STRUCTURE INDEX OF SAND

One structure index for sands may be defined as: Structure Index $I_F$, $$I_F = (F - 3)A \quad (23)$$

Figure 11:
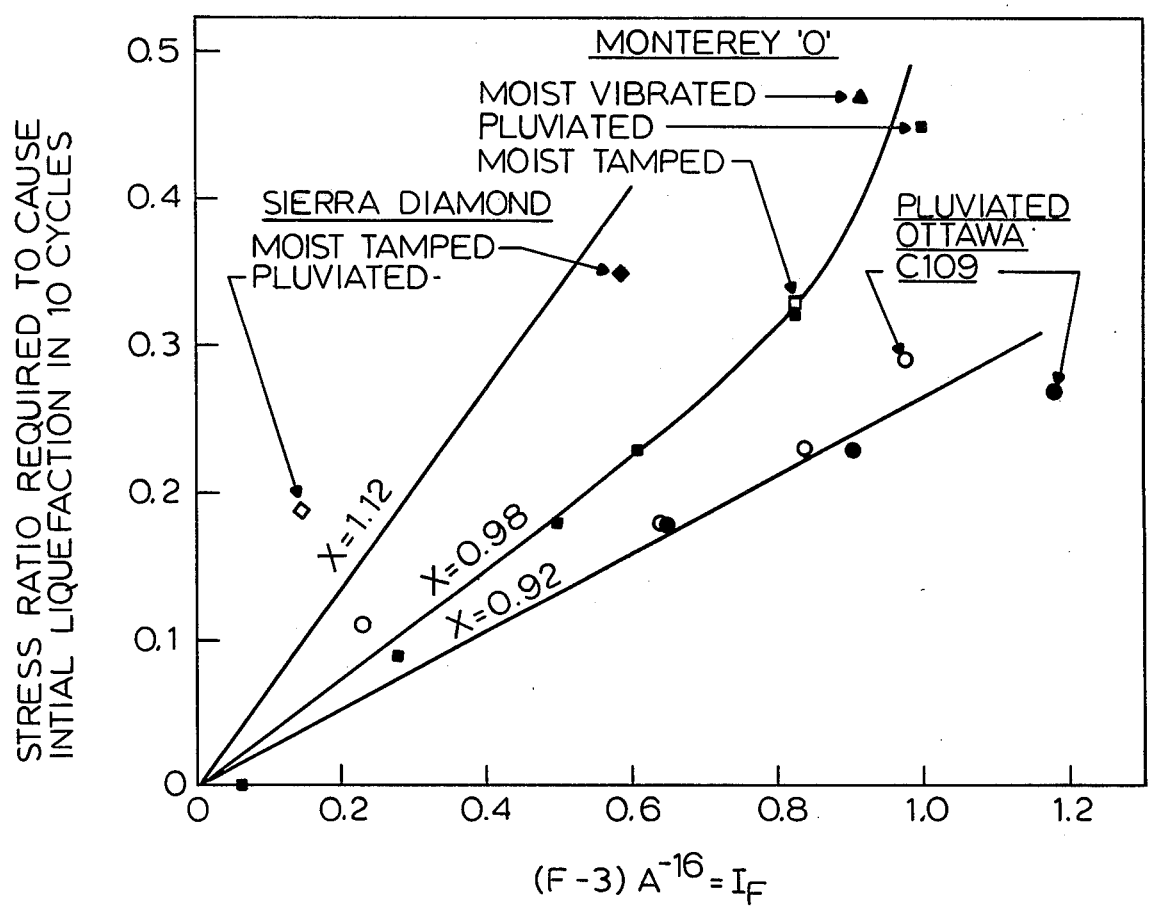
FIG. 11 is a graph plotting the stress ratio required to cause initial liquefaction in ten cycles against the structure index $I_F$ defined as $(F-3) A^{-16}$.

It is therefore possible to examine the correlation between this structure index and the liquefaction behavior of sands. The results presented in FIG. 11 plot the stress ratio required to cause initial liquefaction in ten cycles (vertical) against $I_F$, with A being modified to reduce the magnitude of the number, as $A^{-16}$. X expresses the shape. Similar relationships for other sands can be used to predict the stress ratio required to cause liquefaction.

Another structure index $I_{DR}$ is related to relative density and is defined as:

$$I_{DF} = D_r A^{-16} \tag{24}$$

6. Prediction of Friction Angle from In Situ Measurements

Earlier relationship of formation factor to friction angle was established from results on one sand. Recently, other sands have been tested and a new general relationship discovered. The equation relating formation factor and shape of particles to friction angle is $$\phi = 13.33 FX - 10.33 \tag{25}$$

Thus by measuring F and X in field $\phi$ can be predicted.

7. Relationship between Structure Index, Shape Factor, and Stress Ratio Required to Cause Initial Liquefaction in 10 Cycles The results of numerous studies have confirmed that the initial liquefaction behavior of saturated sands is influenced primarily by soil type and gradation, porosity, strain history, the initial effective confining pressure for a given intensity and duration of shaking. At a given strain history, initial effective confining pressure, and for a given intensity and duration of shaking, particle size, shape, and gradation have a great influence on liquefaction characteristics of sands. The influence of size, shape, and gradation characteristics of sand at a given porosity is characterized by its relative density.

different dynamic modulus and damping characteristics, and different compressibility characteristics. Thus, the potential significance of factors other than density in producing changes in liquefaction characteristics has been given important support and clearly warrants consideration in any design study of liquefaction potential.

Thin section studies on Monterey 'O' sand prepared by different methods show that moist vibrated samples at 50 percent relative density have a nearly random distribution of long axis orientations. Definite preferred orientation of long axes in a direction normal to the longitudinal axis was developed by pluviation. The formation factor values measured in the vertical direction, $F_V$, are also in increasing order for moist vibrated, moist tamped or pluviated samples at a given relative density. It appears that for a given relative density the greater the intensity of preferred long axis orientation in a direction normal to the direction of the applied cyclic deviator stress, the less resistance to liquefaction under triaxial loading conditions.

The facts that an electrical anisotropy coefficient, $$A = \sqrt{F_V/F_H} \tag{16}$$

can be measured and that the electrical parameter F is affected by preferred long axis orientations suggest that A is a measure of particle orientation. It has been shown that particle orientation as well as relative density and shape effect the stress ratio required to cause initial liquefaction, therefore a relationship between A, $D_r$, the shape factor X, and the stress ratio required to cause initial liquefaction for three different sands (Ottawa C109, Monterey 'O', and Sierra Diamond) was developed and is tabulated in Table 2. These relationships are for three uniformly graded sands with different shapes.

TABLE 2

STRESS RATIO AND STRUCTURE INDICES FOR SANDS TESTED

| Sand | Method of Preparation | Porosity $\eta$ | Relative Density $D_r$ | Stress Ratio* | Average Formation Factor F | Anisotropy Index A | Structure Index $I_{DR} = D_r(A)^{-16}$ |
|---|---|---|---|---|---|---|---|
| Monterey 'D' | Pluviated | 0.375 | 85 | 0.45 | 4.30 | 1.016 | 66 |
| | " | 0.390 | 70 | 0.32 | 4.08 | 1.016 | 54 |
| | " | 0.420 | 40 | 0.18 | 3.65 | 1.016 | 31 |
| | " | 0.440 | 20 | 0.09 | 3.36 | 1.016 | 15 |
| | " | 0.460 | 0 | 0 | 3.08 | 1.016 | 0 |
| | " | 0.410 | 50 | 0.23 | 3.79 | 1.016 | 39 |
| | Moist Tamped | 0.410 | 50 | 0.33 | 3.75 | 0.994 | 55 |
| | Moist Vibrated | 0.410 | 50 | 0.47 | 3.69 | 0.982 | 67 |
| Ottawa C109 | Pluviated | 0.375 | 69 | 0.29 | 4.08 | 1.006 | 63 |
| | " | 0.385 | 61 | 0.23 | 3.93 | 1.006 | 55 |
| | " | 0.400 | 50 | 0.18 | 3.70 | 1.006 | 45 |
| | " | 0.430 | 23 | 0.11 | 3.25 | 1.006 | 21 |
| | " | 0.360 | 75 | 0.27 | 4.30 | 1.006 | 68 |
| | " | 0.380 | 65 | 0.23 | 4.00 | 1.006 | 59 |
| | " | 0.400 | 45 | 0.18 | 3.70 | 1.006 | 41 |
| Sierra | Pluviated | 0.440 | 40 | 0.19 | 3.3 | 1.042 | 21 |
| | Moist Tamped | 0.440 | 40 | 0.35 | 3.5 | 0.990 | 47 |

*Stress ratio required to cause initial liquefaction in 10 cycles

The importance of factors other than density on the liquefaction characteristics of sand has been reported by many investigators. Some have showed that the liquefaction characteristics were influenced by the strain history to which they have been subjected. Recent studies show that samples of a given sand prepared to the same density by different methods may have different settlement characteristics, different liquefaction characteristics, different structures, different penetration resistances, different permeability characteristics, To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

I claim:

1. Apparatus for measuring in situ the resistance and capacitance at radio frequency of soils, including sands and silts, to enable evaluation of the density and fabric thereof, comprising:

probe means adapted to be driven into the soil to be measured in situ to a fixed depth so that said probe means comes into physical proximity and electrical contact with a sample of said soil to be evaluated, said probe means having a first pair of electrodes for measuring in situ the electrical resistance and capacitance of said soil sample along a horizontal direction, a second pair of electrodes for measuring in situ the electrical resistance and capacitance along a vertical direction, a pore-liquid chamber in said probe means having an inlet and means for relieving gas, a third pair of electrodes in said pore liquid for measuring in situ the electrical resistance and capacitance of pore liquid in said chamber, filter means at the inlet to said probe means for admitting pore liquid to said chamber and excluding the soil therefrom, means for applying radio-frequency voltage to each said pair of electrodes, resistance measurement indicator means in communication with said probe means for indicating said measured resistance of said soil sample along said horizontal direction and along the vertical direction and for indicating the measured resistance of said pore liquid, and capacitance measurement indicator means connected to said probe means for indicating said measured capacitance of said soil sample along the horizontal direction and along the vertical direction and for indicating the measured capacitance of said pore liquid.

2. The apparatus of claim 1 wherein said probe means includes, a radio-frequency bridge adapted for simultaneous in situ measurement of capacitance and resistance of said soil sample, and balancing means for balancing said bridge while it is in place in situ for making said measurements.

3. The apparatus of claim 2 wherein said bridge is a radio frequency capacitance bridge.

4. The apparatus of claim 1 having temperature sensing means in said probe means and indicator means in communication therewith for indicating the sensed temperature.

5. Apparatus for simultaneous measurement in situ of the resistance and capacitance of soils, sands, silts, and the like to enable evaluation of density and fabric thereof, said apparatus comprising probe head means, measurement point means, and interconnection means for electrically interconnecting said probe head means with said measurement point means, said probe head means being adapted to be driven into the soil to be tested to a fixed depth, and including:

a sensor element of plural electrodes for physically engaging a soil sample of the soil to be tested at said fixed depth, an oscillator outputting a signal at a predetermined radio frequency, an impedance bridge including:

a first coil having a primary winding connected to said oscillator and a center tapped secondary winding with one end thereof connected to one of the electrodes of said sensor element, a second coil having a center tapped primary winding with the center tap thereof connected to the center tap of the secondary winding of said first coil, and with one of the ends of said center tapped primary winding being connected to another of the electrodes of said sensor element, said second coil having a secondary winding providing an output of said probe head means, a variable resistance element of adjustable value connected between the other end of said first coil and the other end of said second coil, a variable capacitance element of adjustable value connected between the other end of said first coil and the other end of said second coil, said measurement point means being remote from said probe head means, and including:

signal converting means connected through said interconnection means to said secondary winding of said second coil, for converting said radio frequency signal into a rectified and amplified signal proportional in magnitude to said radio frequency signal, filter means connected to said converter means for smoothing said rectified signal into d.c. voltages, analog to digital converter means connected to said filter means for converting said d.c. voltages into digital values, digital computer means connected to said analog to digital converter means for automatically repeatedly determining from said digital values changes of value of said variable resistance element and said variable capacitance element to provide a null point in said bridge, and providing a digital output change signal, said probe head means further including:

output decoder means connected through said interconnection means to said digital computer means for decoding said digital output change signal, resistance switching means in said variable resistance element connected to said output decoder means, for increasing and decreasing the resistance of said variable resistance element in accordance with said decoded change signal, and capacitance switching means in said variable capacitance element connected to said variable capacitance element connected to said output decoder means for increasing and decreasing the capacitance of said variable capacitance element in accordance with said decoded change signal, said measurement point means further including:

resistance indicator means connected to said digital computer means for indicating soil sample resistance in accordance with the status of said variable resistance element at null point of said bridge, capacitance indicator means connected to said digital computer means for indicating soil sample capacitance in accordance with the status of said variable capacitance element at null point of said bridge, whereby when said probe head means is driven into the soil to be tested and said sensor element comes into physical proximity and electrical contact with a sample of said soil at said fixed depth, and said bridge is then automatically nulled by operation of said computer, resistance and capacitance of said soil sample may thereupon be measured in situ and be read remotely therefrom, thereby enabling evaluation of density and fabric of said soil.

6. The apparatus of claim 5 wherein said plural electrodes comprise one pair of electrodes disposed in horizontal relation to each other and a pair of electrodes disposed in vertical relation to each other, and switching means for placing one said pair at a time in the operation mode, whereby both resistance and capacitance of said soil are determined in both a horizontal direction and in a vertical direction.

7. The apparatus of claim 5 or 6 wherein said probe means includes pore-liquid sensor means for measuring in situ resistance and capacitance of a pore-liquid sample collected at said pore-fluid sensor, said pore-liquid sensor means comprises filter means for passing pore liquid and blocking particulate material and structure defining a chamber having an opening communicating with said filter means, and pore-liquid electrode means in said chamber for contacting said pore liquid collected therein, and thereby enabling measurement by said probe means of resistance and capacitance of said pore-fluid sample, said probe means including switch means for switching between said soil sample measuring plural electrodes and said pore-liquid electrode means.

8. The apparatus of claim 7 wherein said structure includes vent means for venting gas in said chamber to the outside of said probe means, as said pore fluid sample enters said chamber.

9. The apparatus of claim 7 wherein said structure includes an expandable enclosure connected to said chamber and into which gas may pass from said chamber.

10. The apparatus of claim 7 wherein said filter means comprises porous stone material.

11. The apparatus of claim 7 wherein said filter means comprises cotton padding.

12. The apparatus of claim 5 wherein said probe means includes temperature sensor means for measuring in situ the temperature of said soil sample and means connecting said sensor means to said computer.

13. Apparatus for measuring in situ the resistance and capacitance at radio frequency of soils, including sands and silts, to enable evaluation of density and fabric thereof, said apparatus comprising probe head means, control point means, and interconnection means for electrically interconnecting said probe head means with said control point means,
said probe head means adapted for being driven into the soil to be tested to a fixed depth and including:
a sensor element,
an oscillator providing a radio-frequency current output signal at a predetermined frequency and amplitude,
a bridge circuit connected to said sensor element and to said oscillator,
said bridge including a variable resistor and a variable capacitor in electrical connection therewith, remotely controllable resistor adjusting means for adjusting said resistor, and remotely controllable capacitor adjusting means for adjusting said capacitor,
said control point means including:
resistance setting means connected through said interconnection means to said remotely controllable resistor adjusting means for setting the adjustment of said resistor,
capacitance setting means connected through said interconnection means to said remotely controllable capacitor adjusting means for setting the adjustment of said capacitor,
null point indicator means connected through said interconnection means to said capacitance bridge, for indicating a null point of said bridge,
resistance indication means correlated to the setting of said resistor for indicating soil sample resistance in accordance with the setting of said resistor upon indication of null point of said bridge,
capacitance indication means correlated to the setting of said capacitor for indicating soil sample capacitance in accordance with the setting of said capacitor upon indication of null point of said bridge,
whereby when said probe head means is driven into the soil to be tested and said sensor element comes into physical proximity and electrical contact with a sample of said soil at said fixed depth, and said bridge is balanced by adjustment at said control point means of said variable resistor and said variable capacitor, the resistance and capacitance of said coil sample at radio frequency may be measured in situ, thereby enabling evaluation of density and fabric thereof.

14. Apparatus for simultaneous measurement in situ of the resistance and capacitance at radio frequency of soils, including sands and silts, to enable evaluation of density and fabric thereof, said apparatus comprising probe head means, control point means, and interconnection means for electrically interconnecting said probe head means with said control point means,
said probe head means being adapted to be driven into the soil to be tested to a fixed depth and including:
a sensor element,
an oscillator providing a radio-frequency current output signal at a predetermined frequency and amplitude,
a capacitance bridge circuit connected to said sensor element and to said oscillator,
said bridge including an incrementally variable resistance element and an incrementally variable capacitance element in electrical connection therewith,
radio-frequency current detector means connected to said bridge for detecting the magnitude of radio-frequency current therein,
incremental resistance adjustment means connected to said detector means and to said resistance element for automatically incrementing and decrementing said resistance element in accordance with the magnitude of detected alternating current in said bridge until a null point is reached whereupon said resistance adjustment means ceases action,
incremental capacitance adjustment means connected to said detector means and to said capacitance element for automatically incrementing and decrementing said capacitance element in accordance with the magnitude of said detected alternating current in said bridge until a null point is reached whereupon said capacitance adjustment means ceases action,
said control point means being remote from said probe head means and including:
automatic control means for automatically controlling simultaneously said incremental resistance adjustment means to bring about said null point and then cease control,
resistance measurement indication means connected to said incremented resistance adjustment means for indicating soil resistance when said bridge is at null point, capacitance measurement indication means connected to said incremental capacitance adjustment means for indicating soil capacitance when said bridge is at null point, whereby when said probe head means is driven into the soil to be tested and said sensor element comes into physical proximity and electrical contact with a sample of said soil at said fixed depth, and said bridge is automatically balanced, the resistance and capacitance at radio frequency of said soil sample may thereupon be measured in situ and be displaced remotely therefrom, thereby enabling evaluation of density and fabric of said soil.

15. The apparatus of claim 14 further comprising manual override control means at said control point means, said manual control means being engageably connected to said incremental resistance adjustment means and to said incremental capacitance adjustment means for enabling manual adjustment thereof to a null point, and null point monitor means at said control point means in connection with said detector means for indicating said null point.

16. Apparatus for simultaneous measurement in situ of the resistance and capacitance of soils, sands, silts, and the like to enable evaluation of density and fabric thereof, said apparatus comprising probe head means, measurement point means, and interconnection means for electrically interconnecting said probe head means with said measurement point means, said probe head means being adapted to be driven into the soil to be tested to a fixed depth, and including:

a sensor element of plural electrodes for physically engaging a soil sample of the soil to be tested at said fixed depth, a first oscillator outputting a signal at a predetermined radio frequency, a second oscillator outputting a signal at a predetermined modulating frequency, a modulator connected to said first oscillator and to said second oscillator for modulating said radio frequency signal with said modulating frequency signal, to provide a modulated radio frequency signal as output, an impedance bridge including:

a first coil having a primary winding connected to said modulator and a center tapped secondary winding with one end thereof connected to one of the electrodes of said sensor element, a second coil having a center tapped primary winding with the center tap thereof connected to the center tap of the secondary winding of said first coil, and with one of the ends of said center tapped primary winding being connected to another of the electrodes of said sensor element, said second coil having a secondary winding providing an output of said probe head means, a variable resistance element of incrementally adjustable value connected between the other end of said first coil and the other end of said second coil, a variable capacitance element of incrementally adjustable value connected between the other end of said first coil and the other end of said second coil, said measurement point means remote from said probe head means, and including:

radio frequency amplifier means connected through said interconnection means to said secondary winding of said second coil, for amplifying said modulated radio frequency signal, rectifier means connected to said radio frequency amplifier means for rectifying said modulated radio frequency signal to recover said modulating signal, filter means connected to said rectifier means for smoothing said rectified modulating signal into d.c. voltages, analog to digital converter means connected to said filter means for converting said d.c. voltages into digital values.

digital computer means connected to said analog to digital converter means for automatically repeatedly determining from said digital values incremental changes of value of said variable resistance element and said variable capacitance element to provide a null point in said bridge, and providing a digital output change signal, said probe head means further including:

output decoder means connected through said interconnection means to said digital computer means for decoding said digital output change signal, incremental resistance switching means in said variable resistance element connected to said output decoder means, for incrementing and decrementing said variable resistance element in accordance with said decoded change signal, incremental capacitance switching means in said variable capacitance element connected to said output decoder means, for incrementing and decrementing said variable capacitance element in accordance with said decoded change signal, said measurement point means further including:

resistance indicator means connected to said digital computer means for indicating soil sample resistance in accordance with the status of said variable resistance element at null point of said bridge, capacitance indicator means connected to said digital computer means for indicating soil sample capacitance in accordance with the status of said variable capacitance element at null point of said bridge, whereby when said probe head means is driven into the soil to be tested and said sensor element comes into physical proximity and electrical contact with a sample of said soil at said fixed depth, and said bridge is then automatically nulled by operation of said computer, resistance and capacitance of said soil sample may thereupon be measured in situ and be read remotely therefrom, thereby enabling evaluation of density and fabric of said soil.

17. The apparatus of claim 16 further comprising manual override control means at said measurement point means, said manual control means being engageably connected to said incremental resistance switching means and to said incremental capacitance switching means for enabling manual adjustment thereof to a null point, and null point monitor means at said measurement point means in connection with said rectifier means for indicating said null point.

18. The apparatus of claim 16 wherein said sensor comprises two pairs of electrodes, one disposed in horizontal relation to each other and the other diposed in vertical relation to each other.

19. The apparatus of claim 16 wherein said probe means includes pore-liquid collection means for collecting soil-free pore liquid and pore-liquid sensor means for measuring in situ the resistance of the collected pore liquid.

20. The apparatus of claim 19 wherein said pore-liquid collection means comprises filter means for passing pore fluid and blocking particulate material and structure defining a chamber having an opening communicating with said filter means and said pore-liquid sensor means comprises electrodes in said chamber for contacting said collected pore liquid, thereby enabling measurement by said probe means of the resistance and capacitance of said collected pore liquid.

21. The apparatus of claim 20 wherein said structure includes vent means for venting gas in said chamber to the outside of said probe means, as said pore liquid enters said chamber.

22. The apparatus of claim 20 wherein said structure includes an expandable enclosure for receiving gas and relieving it from said chamber as said pore liquid enters said chamber.

23. The apparatus of claim 20 wherein said filter means comprises porous stone material.

24. The apparatus of claim 20 wherein said filter is cotton padding.

25. The apparatus of claim 19 wherein said probe means includes switch means for switching between said soil sample measuring electrodes and said pore liquid sensor means.

26. The apparatus of claim 16 wherein said probe means includes temperature sensor means for measuring in situ the temperature of said soil sample.

27. Apparatus for simultaneous measurement in situ of the resistance and capacitance of soils, sands, silts, and the like to enable evaluation of density and fabric thereof, said apparatus comprising probe head means, measurement point means, and interconnection means for electrically interconnecting said probe head means with said measurement point means, said probe head means being adapted to be driven into the soil to be tested to a fixed depth, and including:
a sensor element of plural electrodes for physically engaging a soil sample of the soil to be tested at said fixed depth,
a first oscillator outputting a signal at a predetermined radio frequency,
an impedance bridge including:
a first coil having a primary winding connected to said first oscillator and a center tapped secondary winding with one end thereof connected to one of the electrodes of said sensor element,
a second coil having a center tapped primary winding with the center tap thereof connected to the center tap of the secondary winding of said first coil, and with one of the ends of said center tapped primary winding being connected to another of the electrodes of said sensor element, said second coil having a secondary winding providing an output of said probe head means,
a variable resistance element of incrementally adjustable value connected between the other end of said first coil and the other end of said second coil,
a variable capacitance element of incrementally adjustable value connected between the other end of said first coil and the other end of said second coil,
a second oscillator outputting a frequency lower than that of said first oscillator by a frequency difference between about 50 to about 500 kHz,
mixing means connected to the output from said second oscillator and to the secondary winding of said second coil for mixing the signals therefrom and for producing a difference signal between about 50 to about 500 kHz,
amplifier means connected to said mixing means for amplifying said difference signal, and
detector means connected to said amplifier means for isolating and putting out said difference frequency,
said measurement point means remote from said probe head means, and including:
rectifier means connected through said interconnection means to said detector means for rectifying said difference signal,
filter means connected to said rectifier means for smoothing said rectified difference signal into d.c. voltages,
analog to digital converter means connected to said filter means for converting said d.c. voltages into digital values,
digital computer means connected to said analog to digital converter means for automatically repeatedly determining from said digital values incremental changes of value of said variable resistance element and said variable capacitance element to provide a null point in said bridge, and providing a digital output change signal,
said probe head means further including:
output decoder means connected through said interconnection means to said digital computer means for decoding said digital output change signal,
incremental resistance switching means in said variable resistance element connected to said output decoder means, for incrementing and decrementing said variable resistance element in accordance with said decoded change signal,
incremental capacitance switching means in said variable capacitance element connected to said output decoder means, for incrementing and decrementing said variable capacitance element in accordance with said decoded charge signal,
said measurement point means further including:
resistance indicator means connected to said digital computer means for indicating soil sample resistance in accordance with the status of said variable resistance element at null point of said bridge,
capacitance indicator means connected to said digital computer means for indicating soil sample capacitance in accordance with the status of said variable capacitance element at null point of said bridge,
whereby when said probe head means is driven into the soil to be tested and said sensor element comes into physical proximity and electrical contact with a sample of said soil at said fixed depth, and said bridge is then automatically nulled by operation of said computer, resistance and capacitance of said soil sample may thereupon be measured in situ and be read remotely therefrom, thereby enabling evaluation of density and fabric of said soil.

28. The apparatus of claim 27 further comprising manual override control means at said measurement point means, said manual control means being engageably connected to said incremental resistance switching means and to said incremental capacitance switching means for enabling manual adjustment thereof to a null point, and null point monitor means at said measurement point means in connection with said rectifier means for indicating said null point.

29. The apparatus of claim 27 wherein said probe means includes pore-liquid collecting means for collecting soil-free pore liquid from said soil and pore-liquid sensor means for measuring in situ the resistance of the collected pore liquid.

30. The apparatus of claim 29 wherein said pore-liquid collecting means comprises filter means for passing pore fluid and blocking particulate material and structure defining a chamber having an opening communicating with said filter means and said pore-liquid sensor means comprises electrodes in said chamber for contacting said collected pore liquid, thereby enabling measurement by said probe means of the resistance and capacitance of said collected pore liquid.

31. The apparatus of claim 30 wherein said structure includes vent means for venting gas in said chamber to the outside of said probe means, as the pore-liquid sample enters said chamber.

32. The apparatus of claim 30 wherein said structure includes an expandible second chamber for receiving gas and relieving the gas from said first-named chamber as said pore liquid enters said first-named chamber.

33. The apparatus of claim 30 having an electrically actuated, normally closed valve for admitting pore liquid from said soil into said chamber.

34. The apparatus of claim 29 wherein said probe means includes switch means for switching between said soil sample measuring electrodes and said pore-liquid sensor means.

35. The apparatus of claim 27 wherein said probe means includes temperature sensor means for measuring in situ the temperature of said soil sample.

36. The apparatus of claim 27 wherein said sensor comprises two pairs of electrodes, one disposed in horizontal relation to each other and the other disposed in vertical relation to each other.

37. A method of evaluating in situ mechanical properties of soils, including sands and silts, from certain electrical properties thereof, comprising forcing into said soil two pairs of spaced-apart electrodes, so that some of the in situ soil to be measured lies between said electrodes, one said pair of electrodes being disposed horizontally and the other being disposed vertically in said soil, sending a radio-frequency current across said electrodes, measuring at said radio frequency the electrical resistance and capacitance of the soil across each said pair of said electrodes to obtain the horizontal resistance, vertical resistance, horizontal capacitance and vertical capacitance of said soil in situ, filtering in situ pore liquid from said soil at a locus adjacent said electrodes to obtain a soil-free pore-liquid sample at that locus, 'sending said radio-frequency current through said pore liquid, measuring at said radio frequency the electrical resistance of said soil-free pore liquid, and calculating from said in situ obtained resistances and capacitances the desired mechanical properties.

38. A method of evaluating in situ mechanical properties of soils, including sands and silts, from certain electrical properties thereof, comprising forcing into said soil two pairs of spaced-apart vertically extending electrodes, so that some of the in situ soil to be measured lies between said electrodes, one said pair of electrodes being disposed horizontally and the other being disposed vertically in said soil, sending a radio-frequency current across said electrodes and through the soil in between them, measuring at said radio frequency the electrical resistance and capacitance of the soil across both said pairs of said electrodes to obtain the horizontal resistance, vertical resistance, horizontal capacitance and vertical capacitance of said soil in situ, filtering in situ pore liquid from said soil at a locus near said electrodes to obtain a soil-free pore-liquid sample at that locus, sending said radio-frequency current through said soil-free pore liquid, measuring at said radio frequency the electrical resistance of said soil-free pore liquid, and calculating from said in situ obtained resistances and capacitances the density, friction angle, and structural index of said soil.

39. A method of evaluating in situ certain mechanical properties of a selected wet soil, comprising the steps of:

inserting to a predetermined depth into the soil to be tested a probe having spaced-apart soil-sensing electrodes and having a pore-liquid chamber with a soil-filtering inlet thereinto and spaced-apart liquid-sensing electrodes therein, driving said soil-sensing electrodes into said soil to be evaluated so that some of the soil lies in between said soil-sensing electrodes, filling said pore-liquid chamber with filtered pore liquid obtained from said soil near said electrodes, measuring both the resistance and the capacitance of the wet soil in between said soil-sensing electrodes, converting the measured resistance and capacitance of said in-situ soil into the conductivity and the dielectric constant E' therefor, measuring the conductivity and the dielectric constant Es of the pore liquid in said chamber, determining the dielectric constant Er of the dry soil particles, determining the dielectric constant Es of the pore liquid, determining the formation factor F of the wet soil in accordance with the formula:

$$F = \frac{\text{conductivity of pore liquid between liquid-sensing electrodes}}{\text{conductivity of wet soil between soil-sensing electrodes}}, \text{ and}$$

then determining the soil porosity n from the formula:

$$n = F\left(\frac{E' - Er}{Es - Er}\right)^2.$$

40. The method of claim 39 including the step of calculating the in situ density n by the formula:

$$n = (2/1 + F).$$

41. The method of claim 40 including the step of calculating a factor X related to the shape of the said particles, using the formula:

$$X = Fn - 1/1 - n.$$

42. The method of claim 41 including the step of calculating the friction angle $\phi$ of the soil from the formula:

$$\phi = 13.33\, FX - 10.33.$$

43. The method of claim 39 including the step of calculating the relative density in the field, $D_r$ as from the formula:

$$D_r = F - 3/1.8.$$

44. The method of claim 39 wherein a coefficient of anisotropy A is obtained by
determining the conductivity of the soil between said sensing electrodes along an horizontal plane, determining therefrom a value $F_H$,
determining the conductivity of the soil between soil-sensing electrodes along a vertical plane, determining therefrom a value $F_V$ and then calculating $$A = \sqrt{F_V/F_H}.$$

45. The method of claim 44 including the step of calculating the relative density $D_r$ from the formula:

$$D_r = F - 3/1.8,$$

and then calculating a structural index $I_{D_r}$ from the formula:

$$D_{D_r} = D_r A^{-16}.$$

46. A method of evaluating in situ certain mechanical properties of a selected wet soil, of which the dielectric constant Er of the dry soil particles and the dielectric constant Es of the pore liquid thereof are known, comprising the steps of:
emplacing into said selected soil, in situ, spaced-apart soil-sensing electrodes, so that some of said soil lies in between said soil-sensing electrodes,
emplacing into said selected soil, in situ and near said electrodes, a pore-liquid chamber having a soil-filtering inlet thereinto and having spaced-apart liquid-sensing electrodes therein,
filling said pore-liquid chamber with filtered pore liquid so that pore liquid lies in between said liquid-sensing electrodes,
sending radio-frequency current across the soil-sensing electrodes,
measuring both the resistance and the capacitance of the wet soil in between said soil-sensing electrodes,
converting the measured resistance and capacitance of said in situ wet soil into the conductivity and the dielectric constant E' therefor,
sending radio-frequency current across the liquid-sensing electrodes,
measuring the resistance of the pore liquid in said chamber,
converting the measured resistance of the pore liquid into the conductivity thereof,
determining the formation factor F of the wet soil in accordance with the formula:

$$F = \frac{\text{conductivity of pore liquid between liquid-sensing electrodes}}{\text{conductivity of wet soil between soil-sensing electrodes}},$$

and then
determining the soil's porosity n from the formula:

$$n = F\left(\frac{E' - Er}{Es - Er}\right)^2.$$

47. The method of claim 46 wherein the frequency of the radio-frequency current is about one megaHertz.

48. The method of claim 46 including the step of calculating in situ said density n by the formula:

$$n = (2/1 + F).$$

49. The method of claim 48 including the step of calculating a factor X related to the shape of the said particles using the formula:

$$X = Fn - 1/1 - n.$$

50. The method of claim 49 including the step of calculating the friction angle $\phi$ of the soil from the formula:

$$\phi = 13.33\, FX - 10.33.$$

51. The method of claim 46 including the step of determining the relative density in the field, $D_r$ from the formula:

$$D_r = F - 3/1.8.$$

52. The method of claim 46 wherein a coefficient of anisotropy A is obtained by
determining the conductivity of the soil between soil-sensing electrodes along an horizontal plane, determining therefrom a value $F_H$,
determining the conductivity of the soil between soil-sensing electrodes along a vertical plane, determining therefrom a value $F_V$ and then calculating $$A = \sqrt{F_V/F_H}.$$

53. The method of claim 52 including the step of calculating the relative density $D_r$ from the formula:

$$D_r = F - 3/1.8,$$

and
then calculating a structural index $I_{D_r}$ from the formula:

$$I_{D_r} = D_r A^{-16}.$$

54. The method of claim 46 wherein there is the step of determining the degree of saturation of the in situ soil by
determining F for a withdrawn sample of soil that has been 100% saturated with said pore liquid,
determining the actual F for the in situ soil, and
comparing the in situ soil F with the saturated soil F on a logarithm basis.

* * * * *